US010435475B2

(12) United States Patent
Honczarenko et al.

(10) Patent No.: US 10,435,475 B2
(45) Date of Patent: Oct. 8, 2019

(54) METHOD OF USING ANTIBODY POLYPEPTIDES THAT ANTAGONIZE CD40 TO TREAT IBD

(71) Applicant: Bristol-Myers Squibb Company, Princeton, NJ (US)

(72) Inventors: Marek Honczarenko, Princeton, NJ (US); Vaishali Shah, Pennington, NJ (US); Xiaoni Liu, Princeton, NJ (US); Wendy L. Trigona, Princeton, NJ (US); Rong Shi, Princeton, NJ (US); Suzanne J. Suchard, Wilmington, DE (US); Karen D. Price, New Brunswick, NJ (US); Linda M. Gustavson, Princeton, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 349 days.

(21) Appl. No.: 15/118,279

(22) PCT Filed: Mar. 9, 2015

(86) PCT No.: PCT/US2015/019506
§ 371 (c)(1),
(2) Date: Aug. 11, 2016

(87) PCT Pub. No.: WO2015/134988
PCT Pub. Date: Sep. 11, 2015

(65) Prior Publication Data
US 2016/0355596 A1 Dec. 8, 2016

Related U.S. Application Data

(60) Provisional application No. 61/949,876, filed on Mar. 7, 2014.

(51) Int. Cl.
*A61K 39/395* (2006.01)
*C07K 16/28* (2006.01)
*A61K 47/60* (2017.01)
*A61K 39/00* (2006.01)

(52) U.S. Cl.
CPC ......... *C07K 16/2878* (2013.01); *A61K 47/60* (2017.08); *A61K 2039/505* (2013.01); *A61K 2039/54* (2013.01); *A61K 2039/545* (2013.01); *C07K 2317/21* (2013.01); *C07K 2317/33* (2013.01); *C07K 2317/35* (2013.01); *C07K 2317/52* (2013.01); *C07K 2317/53* (2013.01); *C07K 2317/569* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,182,368 A | 1/1993 | Ledbetter et al. | |
| 5,247,069 A | 9/1993 | Ledbetter et al. | |
| 5,674,492 A | 10/1997 | Armitage et al. | |
| 5,677,165 A | 10/1997 | de Boer et al. | |
| 5,786,456 A | 7/1998 | Ledbetter et al. | |
| 5,849,898 A | 12/1998 | Seed et al. | |
| 5,916,560 A | 6/1999 | Larsen et al. | |
| 6,051,228 A | 4/2000 | Aruffo et al. | |
| 6,056,959 A | 5/2000 | de Boer et al. | |
| 6,376,459 B1 | 4/2002 | Aruffo et al. | |
| 8,669,352 B2 | 3/2014 | den Hartog et al. | |
| 8,828,396 B2 | 9/2014 | Heusser et al. | |
| 9,475,879 B2 | 10/2016 | Suri et al. | |
| 2006/0062784 A1 | 3/2006 | Grant et al. | |
| 2006/0233797 A1* | 10/2006 | Gujrathi .............. | A61K 31/56 424/144.1 |
| 2007/0148163 A1 | 6/2007 | Takahashi et al. | |
| 2013/0011405 A1* | 1/2013 | Long .................... | A61K 39/395 424/139.1 |
| 2014/0099317 A1 | 4/2014 | Suri et al. | |

FOREIGN PATENT DOCUMENTS

| | | |
|---|---|---|
| AU | 2012245309 C1 | 2/2016 |
| CL | 199900284 | 9/1999 |
| CL | 200700768 | 11/2007 |
| CL | 200701105 | 11/2007 |
| CL | 200701335 | 1/2008 |
| CL | 200901779 | 2/2010 |
| CL | 201202737 | 2/2013 |
| CL | 201301124 | 7/2014 |

(Continued)

OTHER PUBLICATIONS

Rudikoff et al, Proc Natl Acad Sci USA 79: 1979-1983 (1982). (Year: 1982).*
Colman, Research in Immunology 145: 33-36 (1994). (1449; #2 (Year: 1994).*
Kussie et al., J. Immunol. 152: 146-152 (1994) . (Year: 1994).*
Chen et al., EMBO J., 14: 2784-2794 (1995). (Year: 1995).*
Vonderheide et al., Clin Cancer Res 19: 1035-1043 (2013) (Year: 2013).*
Jefferis, Nature Reviews / Drug Discovery 8: 226-234 (2009) (Year: 2009).*
Andrew B. Adams, et al., "Development of a Chimeric Anti-CD40 Monoclonal Antibody That Synergizes with LEA29Y to Prolong Islet Allograft Survival," The Journal of Immunology 2005; 174:542-550.

(Continued)

*Primary Examiner* — Phillip Gambel
(74) *Attorney, Agent, or Firm* — Drinker Biddle & Reath LLP

(57) ABSTRACT

A method of treating an inflammatory bowel disease is provided. The method comprises administration of an antibody polypeptide that specifically binds a novel epitope of human CD40. The antibody polypeptides do not exhibit CD40 agonist activity. The antibody polypeptides may be fusions of a domain antibody (dAb) comprising a single $V_L$ or $V_H$ domain and an Fc domain.

16 Claims, 5 Drawing Sheets

Specification includes a Sequence Listing.

(56) References Cited

FOREIGN PATENT DOCUMENTS

| | | |
|---|---|---|
| CN | 1922316 A | 2/2007 |
| CN | 101061140 A | 10/2007 |
| EP | 1 707 627 A1 | 10/2006 |
| EP | 2255828 A1 | 12/2010 |
| JP | 2008-513425 A | 5/2008 |
| JP | 2009-022289 A | 2/2009 |
| KR | 2006-0130615 A | 12/2006 |
| KR | 10-2013-7030492 B1 | 5/2017 |
| WO | WO-99/20749 A1 | 4/1999 |
| WO | WO-02/28481 A2 | 4/2002 |
| WO | WO-2003/040170 A2 | 5/2003 |
| WO | WO-2005/044294 A2 | 5/2005 |
| WO | WO-2005/093074 A1 | 10/2005 |
| WO | WO-2006030220 A1 | 3/2006 |
| WO | WO-2006/073443 A2 | 7/2006 |
| WO | WO-2007/085815 A2 | 8/2007 |
| WO | WO-2007/124299 A2 | 11/2007 |
| WO | WO-2008/149143 A2 | 12/2008 |
| WO | WO-2011/123489 A2 | 10/2011 |
| WO | WO-2012/145673 A1 | 10/2012 |

OTHER PUBLICATIONS

Shuang Bai, et al., "A Guide to Rational Dosing of Monoclonal Antibodies," Clinical Pharmacokinetics 2012, vol. 51, No. 2, pp. 119-135.

Andrew P. Chapman, "PEGylated antibodies and antibody fragments for improved therapy: a review," Advanced Drug Delivery Reviews 54 (2002) pp. 531-545.

Michael L. Connolly, "Analytical Molecular Surface Calculation," J. Appl. Cryst. (1983), 16, pp. 548-558.

Hennie R. Hoogenboom, et al., "Multi-subunit proteins on the surface of filamentous phage: methodologies for displaying antibody (Fab) heavy and light chains," Nucleic Acids Research, vol. 19, No. 15, pp. 4133-4137.

A. Kasran, et al., "Safety and tolerability of antagonist anti-human CD40 Mab ch5D12 in patients with moderate to severe Crohn's disease," Alimentary Pharmacology & Therapeutics 2005, 22: 111-122.

Stuart Rudikoff, et al., "Single amino acid substitution altering antigen-binding specificity," Proceedings of the National Academy of Sciences, Mar. 1982, vol. 79, pp. 1979-1983.

Steven Sheriff, "Some Methods for Examining the Interactions between Two Molecules," Immunomethods 3 (1993) pp. 191-196.

Steven Sheriff, et al., "Structure of Myohemerythrin in the Azidomet State at 1•7/1•3 Å Resolution," J. Mol. Biol. (1987) 197, pp. 273-296.

Karsten Winkler, et al., "Changing the Antigen Binding Specificity by Single Point Mutations of an Anti-p24 (HIV-1) Antibody," The Journal of Immunology, 2000, vol. 165, No. 8, pp. 4505-4514.

Hilde De Winter, et al., "Mucosal Immunity and Inflammation II. The yin and yang of T cells in intestinal inflammation: pathogenic and protective roles in a mouse colitis model," Am. J. Physiol. Gastrointest Liver Physiol. 1999, 276:G1317-G1321.

International Search Report dated May 20, 2015 for PCT/US2015/019506.

Written Opinion dated May 20, 2015 for PCT/US2015/019506.

EP Application No. 15 710 401.9.0, Offical Communication dated Nov. 3, 2017.

EP Application No. 15 710 401.9.0, Offical Communication dated Oct. 21, 2016.

International Preliminary Report on Patentability dated Sep. 13, 2016 for PCT/US2015/019506.

"Study of HCD122 (Lucatumumab) and Bendamustine Combination Therapy in CD40+ Rituximab-Refractory Follicular Lymphoma," Clinical Trials, Jan. 10, 2012 [online]. [retrieved on Jun. 30, 2015]. Retrieved from the Internet <URL:http://clinicaltrials.gov/show/NCT01275209>.

An et al., 2011, "Crystallographic and mutational analysis of the CD4O-CD154 complex and its implications for receptor activation," J Biol Chem. 286(13):11226-35.

Arkin et al., "An algorithm for protein engineering: Simulations of recrusive ensemble mutagenesis", Proc. Nat'l Acad. Sci. USA 89:7811-7815 (1992).

Blanc et al., "Refinement of severly incomplete structures with maximum likelihood in BUSTER-TNT", Acta Cryst. D60: 2210-2221 (2004).

Brand et al., "The Mouse Model of Collagen-Induced Arthritis", in Methods Mol. Med., vol. 102, Humana Press Inc., Totowa New Jersey, pp. 295-312 (2004).

Chen et al., "Enhancement and destruction of antibody function by somatic mutation: unequal occurrence is controlled by V gene combinatorial associations," The EMBO Journal 14(12):2787-2794 (1995).

Colman, "Effects of amino acid sequence changes on antibody-antigen interactions," Res. Immunol. 145(1):33-36 (1994).

Davies et al., "TRAF6 is Required for TRAF2-Dependent CD40 Signal Transduction in Nonhemopoietic Cells", Mol. Cell Biol. 25: 9806-19 (2005).

de Kruif et al., "Rapid selection of cell subpopulation-specific human monoclonal antibodies from a synthetic phage antibody library", Proc. Natl. Acad. Sci. USA 92: 3938 (1995).

Emsley et al., "Coot: model-building tools for molecular graphics", Acta Cryst. D60: 2126-2132 (2004).

Emsley et al., "Features and Development of Coot," Acta Cryst. D66: 486-501 (2010).

Harrison et al., "Screening of Phage Antibody Libraries", Meth. Enzymol. 267: 83-109 (1996).

Kouskoff et al., "Organ-specific disease provoked by systemic autoimmunity", Cell 87: 811-822 (1996).

Kussie et al., "A Single Engineered Amino Acid Subsitution Changes Antibody Fine Specificity," J. Immunol. 152(1):146-152 (1994).

Lawrence et al., "Shape Complementarity at Protein/Protein Interfaces," J. Mol. Biol. 234: 946-950 (1993).

Malmborg Hager, et al., "Affinity and Epitope Profiling of Mouse Anti-CD40 Monoclonal Antibodies," Scandinavian Journal of Immunology, 57, pp. 517-524 (2003).

Marks et al., "Human antibody fragments specific for human blood group antigens from a phage display library", BioTechnology 11: 1145-1149 (1993).

McCoy et al., "Phaser crystallographic software", J. Appl. Crystallogr. 40: 658-674 (2007).

Pape et al., "Use of adoptive transfer of T-cell-antigen-receptor-transgenic T cell for the study of T-cell activation in vivo", Immunol. Rev. 156: 67-78 (1997).

Tronrud et al., "An efficient general-purpose least-squares refinement program for macromolecular structures", Acta Cryst. A43: 489-501 (1987).

Yamniuk et al, "Functdional Antagonism of Human CD40 Achieved by Targeting a Unique Species-Specific Epitope," J Mol Biol. 428:2860-2879 (2016).

Zhuang, et al., "A novel blocking monoclonal antibody recognizing a distinct epitope of human CD40 molecule," Tissue Antigens, 65: 81-87 (2005).

D'Angelo et al., "Many Routes to an Antibody Heavy-Chain CDR3: Necessary, Yet Insufficient, for Specific Binding," Front. Immunol. 9:395 (2018).

Byrd JC et al., "Phase I study of the anti-CD40 humanized monoclonal antibody lucatumumab (HCD122) in relapsed chronic lymphocytic leukemia," Leuk Lymphoma. Nov. 2012, 53(11):2136-42; (Author manuscript, PMCID PMC3808981, Oct. 28, 2013).

Vonderheide RH et al., "Clinical activity and immune modulation in cancer patients treated with CP-870,893, a novel CD40 agonist monoclonal antibody," J Clin Oncol. 2007, 25(7):876-83.

Walpole et al., "The weight of nations: an estimation of adult human mass," BMC Public Health 2012, 12:439.

European Medicines Agency (EMEA). (2007) Guideline on Strategies to identify and mitigate risks for first-in-human clinical trials with investigational medicinal products. EMEA/CHMP/SWP/28367/07.

* cited by examiner

FIG. 1A

BMS3h-56-269 (SEQ ID NO: 1)

EVQLLESGGGLVQPGGSLRLSCAASGFTFRDYEMWWVRQAPGK
GLERVSAINPQGTRTYYADSVKGRFTISRDNSKNTLYLQMNSL
RAEDTAVYYCAKLPFRFSDRGQGTLVTVSS

CDR1, CDR2, and CD3 are are underlined

FIG. 1B

BMS-986090
BMS3h-56-269-IgG$_4$ Fc fusion polypeptide (SEQ ID NO: 5)

EVQLLESGGGLVQPGGSLRLSCAASGFTFRDYEMWWVRQAPGK

GLERVSAINPQGTRTYYADSVKGRFTISRDNSKNTLYLQMNSL

RAEDTAVYYCAKLPFRFSDRGQGTLVTVSSASTESKYGPPCP*P*

*CPAPEFLGGPSVFLFPPKPKDTLMISRTPEVTCVVVDVSQEDP*

*EVQFNWYVDGVEVHNAKTKPREEQFNSTYRVVSVLTVLHQDWL*

*NGKEYKCKVSNKGLPSSIEKTISKAKGQPREPQVYTLPPSQEE*

*MTKNQVSLTCLVKGFYPSDIAVEWESNGQPENNYKTTPPVLDS*

*DGSFFLYSRLTVDKSRWQEGNVFSCSVMHEALHNHYTQKSLSL*

*SLGK*

FIG. 3

FIH Dose Escalation Scheme and Predicted Exposure/RO

| Dose (mg) | Multiples by AUC from previous dose | AUC(INF) (ug*h/mL) | AUC Margin once every two weeks (monkey AUC/[a] human AUC) | Cmax (ug/mL) | Multiples by Cmax from previous dose | Romax (%) | RO168 (%) | RO336 (%) |
|---|---|---|---|---|---|---|---|---|
| 0.5 (SC) | | 0.11 | 2218182 | 0.0039 | | 9.4 | 0.030 | 0.002 |
| 3 (SC) | 8.4X | 0.93 | 262366 | 0.04 | 9.56X | 49.8 | 0.220 | 0.015 |
| 10 (SC) | 11.8X | 11.02 | 22142 | 0.36 | 9.39 X | 90.3 | 2.05 | 0.164 |
| 30 (SC) KLH | 10.1X | 110.9 | 2201 | 1.94 | 5.32X | 98.0 | 25.68 | 2.25 |
| 100 (SC) KLH | 8.3X | 923.2 | 264 | 7.82 | 4.04 X | 99.5 | 98.2 | 82.9 |
| 100 (IV)/ 300 (SC)KLH | 1.5X/ 6.3X | 1429.1/ 5819.5 | 171/ 42 | 29.15/ 24.74 | 3.73X/ 3.16X | 99.9/ 99.8 | 98.7/ 99.6 | 94.7/ 99.4 |
| 750 (IV) | 4.4X | 25695.1 | 9.5 | 218.60 | 7.50X | 100.0 | 99.9 | 99.9 |
| 150 mg weekly x4 (SC)[b] | N/A[c] | 2722[d] | 45 | 22 | N/A | 99.8 | N/A | 99.7[e] |

[a] Monkey exposure based on dosing with surrogate domain antibody BMS-986091
[b] Values based on exposure after 4th weekly dose
[c] First multiple dose arm
[d] AUC(0-168) after 4th dose
[e] Based on predose concentration after 4th weekly dose Study Design Schematic

*Based on the interim analyses conducted to confirm/select doses for KLH after 100 mg SC dose, additional dose panel may be added between panels 5 & 8.
**Panels 6 and 7 may be dosed simultaneously.

FIG. 5A

Treatment Administration for SC Dose Panels 1, 2, 3, 4, 5, 7, & 9

| Treatment | Total Daily Dose | Formulation Strength | Number of BMS-986090 Vials |
|---|---|---|---|
| 1 | 0.5 mg SC or placebo | 50 mg/mL | 1 |
| 2 | 3 mg SC or placebo | 50 mg/mL | 1 |
| 3 | 10 mg SC or placebo | 50 mg/mL | 1 |
| 4 | 30 mg SC or placebo | 50 mg/mL | 1 |
| 5 | 100 mg SC or placebo | 50 mg/mL | 1 |
| 7 | 300 mg SC or placebo | 50 mg/mL | 2 |
| 9 | 150 mg SC or placebo | 50 mg/mL | 1 |

FIG. 5B

Treatment Administration for IV Dose Panels 6 and 8

| Treatment | Total Daily Dose | BMS-986090 Target Concentration for Administration (mg/mL) | Infusion Rate (mL/hr) | Infusion Volume (mL) | Infusion Time (min) | Infusion Rate (mg/min) |
|---|---|---|---|---|---|---|
| 6 | 100 mg IV or placebo | 2 | 60 | 50 | 50 | 2 |
| 8 | 750 mg IV or placebo | 15 | 60 | 50 | 50 | 15 |

FIG. 5C

KLH Treatment Administration

| Treatment | Total Daily Dose | Formulation Strength | Number of vials |
|---|---|---|---|
| 4 | 1 mg | 1 mg/mL | 1 |
| 5 | 1 mg | 1 mg/mL | 1 |
| 7 | 1 mg | 1 mg/mL | 1 |

METHOD OF USING ANTIBODY POLYPEPTIDES THAT ANTAGONIZE CD40 TO TREAT IBD

TECHNICAL FIELD

Antibodies and fragments thereof that target CD40, and do not exhibit CD40 agonist activity, compositions comprising the same, and methods of using the same for treatment of diseases involving CD40 activity are provided.

CROSS REFERENCE TO RELATED APPLICATIONS

This application is the National Stage of International Application No. PCT/US2015/019506, filed Mar. 9, 2015, and claims the benefit of U.S. Provisional Application No. 61/949,876, filed Mar. 7, 2014, the entire contents of which are herein incorporated by reference.

SEQUENCE LISTING

The instant application contains a Sequence Listing in ASCII format that is hereby incorporated by reference in its entirety. Said ASCII copy, created on Mar. 9, 2015, is named 200896_522604_sequence_listing.txt and is 21,019 bytes in size.

BACKGROUND

CD40 is a co-stimulatory molecule belonging to the tumor necrosis factor (TNF) receptor superfamily that is present on antigen presenting cells (APC), including dendritic cells, B cells, and macrophages. APCs are activated when CD40 binds its ligand, CD154 (CD40L), on $T_H$ cells. CD40-mediated APC activation is involved in a variety of immune responses, including cytokine production, up-regulation of co-stimulatory molecules (such as CD86), and enhanced antigen presentation and B cell proliferation. CD40 can also be expressed by endothelial cells, smooth muscle cells, fibroblasts, and epithelial cells.

CD40 activation is also involved in a variety of undesired T cell responses related to autoimmunity, transplant rejection, or allergic responses, for example. One strategy for controlling undesirable T cell responses is to target CD40 with an antagonistic antibody. For example, monoclonal antibody HCD122 (Lucatumumab), formerly known as Chiron 1212, is currently in clinical trials for the treatment of certain CD40-mediated inflammatory diseases. See "Study of HCD122 (Lucatumumab) and Bendamustine Combination Therapy in CD40+ Rituximab-Refractory Follicular Lymphoma," Clinical Trials Feeds, on the Internet at hypertext transfer protocol: clinicaltrialsfeeds.org/clinical-trials/show/NCT01275209 (last updated Jan. 11, 2011). Monoclonal antibodies, however, can display agonist activity. For example, the usefulness of the anti-CD40 antibody Chi220 is limited by its weak stimulatory potential. See Adams, et al., "Development of a chimeric anti-CD40 monoclonal antibody that synergizes with LEA29Y to prolong islet allograft survival," J. Immunol. 174: 542-50 (2005).

SUMMARY

Provided is a method of treating an inflammatory bowel disease (IBD) in a patient in need of such treatment, comprising administering to the patient a therapeutically effective amount of the antibody polypeptide disclosed herein.

The IBD can be selected from the group consisting of: colitis, Crohn's disease, and Behcet's disease. Colitis can be selected from the group consisting of: ulcerative colitis, collagenous colitis, lymphocytic colitis, and diversion colitis. In an embodiment, the IBD is ulcerative colitis.

In an aspect, the method of treating inflammatory bowel disease (IBD) in a human patient comprises administering to the patient at least one dose of an antibody polypeptide comprising (1) a variable domain wherein the amino acid sequence of the variable domain comprises BMS3h-56-269 (SEQ ID NO: 1) or differs from the amino acid sequence of BMS3h-56-269 (SEQ ID NO: 1) by up to 5 amino acids and (2) a human Fc domain, and the dose is selected from 0.5 to 750 milligrams (mg) of the antibody polypeptide.

In an embodiment, the administration may be sub-cutaneous and the dose is from 0.5 to 300 milligrams (mg) of the antibody polypeptide. The dose may be selected from 0.5, 3, 10, 30, 100, 150, or 300 mg of the antibody polypeptide. The method may comprise more than one iteration of the administering step. The method may comprise sub-cutaneous administration, where the dose is from 150 to 300 mg of the antibody polypeptide, and the method comprises at least four iterations of the administering step.

In an embodiment, the administration is intravenous and the dose is from 100 to 750 mg of the antibody polypeptide. The dose may be selected from 100 or 750 mg of the antibody polypeptide. The method may comprise more than one iteration of the administering step. The method may comprise sub-cutaneous administration, where the the administration is intravenous and the dose is selected from 100 to 750 mg of the antibody polypeptide.

The method may further comprise administering the the antibody polypeptide is administered in combination with an immunosuppressive/immunomodulatory and/or anti-inflammatory agent. The antibody polypeptide and the immunosuppressive/immunomodulatory and/or anti-inflammatory agent may administered sequentially or may be administered simultaneously. In simultaneous administration, the antibody polypeptide and the immunosuppressive/immunomodulatory and/or anti-inflammatory agent may be comprised in separate compositions, or the antibody polypeptide and the immunosuppressive/immunomodulatory and/or anti-inflammatory agent are formulated in a single composition.

In one aspect of the method of treating an inflammatory bowel disease (IBD) in a human patient, the IBD is selected from the group consisting of: colitis, Crohn's disease and Behcet's disease. The colitis may be selected from the group consisting of ulcerative colitis, collagenous colitis, lymphocytic colitis, and diversion colitis.

In the antibody polypeptide administered in the disclosed method, the human Fc domain may comprise an amino acid sequence selected from SEQ ID NO: 4 or SEQ ID NO: 6. The antibody polypeptide may further comprise a linker selected from the group consisting of: SEQ ID NOS: 8-16.

In an embodiment, the amino acid sequence of the variable domain of the antibody polypeptide differs from the amino acid sequence of BMS3h-56-269 (SEQ ID NO: 1) by up to 5 amino acids. Optionally, the first variable domain has an apparent binding constant of 1 pM to 100 nM (e.g., 1 pM to 10 nM).

In an embodiment, the amino acid sequence of the variable domain of the antibody polypeptide comprises BMS3h-56-269 (SEQ ID NO: 1). In an embodiment, the amino acid sequence of the variable domain of the antibody polypeptide comprises BMS3h-56-269 (SEQ ID NO: 1), and the Fc domain (region) comprises the amino acid sequence of SEQ ID NO: 4. In an embodiment of the method, the antibody polypeptide comprises the amino acid sequence of SEQ ID NO: 5. Optionally, the antibody polypeptide is linked to one or more PEG polymers.

Provided is a kit for treating an inflammatory bowel disease (IBD) in a human patient. The kit comprises (a) a dose of an antibody polypeptide comprising BMS3h-56-269-IgG$_4$ Fc fusion polypeptide (SEQ ID NO: 5), and (b) instructional material for using the antibody polypeptide in the disclosed method of treating an autoimmune disease.

Also provided is a method of treating an inflammatory bowel disease (IBD) by administering an antibody polypeptide where the amino acid sequence of the first variable domain comprises (a) a CDR1 region which differs from the CDR1 region of BMS3h-56-269 (amino acids 31-35 of SEQ ID NO: 1) by up to two amino acids, (b) a CDR2 region which differs from the CDR2 region of BMS3h-56-269 (amino acids 50-66 of SEQ ID NO:1) by up to two amino acids, (c) a CDR3 region which differs from the CDR3 region of BMS3h-56-269 (amino acids 99-105 of SEQ ID NO: 1) by up to two amino acids, (d) a FR1 region which differs from the FR1 region of BMS3h-56-269 (amino acids 1-30 of SEQ ID NO: 1) by up to two amino acids, (e) a FR2 region which differs from the FR2 region of BMS3h-56-269 (amino acids 36-49 of SEQ ID NO: 1) by up to two amino acids, (f) a FR3 region which differs from the FR3 region of BMS3h-56-269 (amino acids 67-98 of SEQ ID NO: 1) by up to two amino acids, and (g) a FR4 region which differs from the FR4 region of BMS3h-56-269 (amino acids 106-116 of SEQ ID NO: 1) by up to two amino acids.

Also provided is a method of treating an inflammatory bowel disease (IBD) by administering an antibody polypeptide where the amino acid sequence of the first variable domain comprises (a) a CDR1 region which differs from the CDR1 region of BMS3h-56-269 (amino acids 31-35 of SEQ ID NO: 1) by up to two amino acids, (b) a CDR2 region which differs from the CDR2 region of BMS3h-56-269 (amino acids 50-66 of SEQ ID NO: 1) by up to two amino acids, (c) a CDR3 region which differs from the CDR3 region of BMS3h-56-269 (amino acids 99-105 SEQ ID NO: 1) by up to two amino acids.

Further provided is a method of treating an inflammatory bowel disease (IBD) by administering an antibody polypeptide where the amino acid sequence of the first variable domain differs from the amino acid sequence of BMS3h-56-269 (SEQ ID NO: 1) by up to 10 amino acids.

Further provided is a method of treating an inflammatory bowel disease (IBD) by administering an antibody polypeptide where the amino acid sequence of the first variable domain differs from the amino acid sequence of BMS3h-56-269 (SEQ ID NO: 1) by up to 5 amino acids.

Further provided is a method of treating an inflammatory bowel disease (IBD) by administering an antibody polypeptide where the amino acid sequence of the first variable domain differs from the amino acid sequence of or BMS3h-56-269 (SEQ ID NO: 1) by two amino acids.

Further provided is a method of treating an inflammatory bowel disease (IBD) by administering an antibody polypeptide where the amino acid sequence of the first variable domain differs from the amino acid sequence of BMS3h-56-269 (SEQ ID NO: 1) by one amino acid.

Further provided is a method of treating an inflammatory bowel disease (IBD) by administering an antibody polypeptide where the first variable domain comprises the amino acid sequence of BMS3h-56-269 (SEQ ID NO: 1).

Further provided is a method of treating an inflammatory bowel disease (IBD) by administering an antibody polypeptide where the variable domain is fused to an Fc domain.

BRIEF DESCRIPTION OF THE FIGURES

FIG. 1, comprising FIGS. 1A and 1B, depicts amino acid sequences of antibody polypeptides useful in the disclosed method. FIG. 1A depicts the amino acid sequence of domain antibody (dAb) BMS3h-56-269 (SEQ ID NO: 1). The three complementarity-determining regions (CDR1, CDR2 and CDR3) are underlined. The amino acids of the four framework regions (FR1, FR2, FR3 and FR4) are not underlined. FIG. 1B depicts the amino acid sequence (SEQ ID NO: 5) of an antibody polypeptide that is a fusion of BMS3h-56-269 and an Fc domain. The antibody polypeptide comprises BMS3h-56-269 linked to human IgG$_4$ Fc domain that is modified; the italicized proline is a serine in the unmodified human IgG$_4$ Fc domain. The dAb amino acid sequence is underlined. The linker amino acid sequence AST is double-underlined. The amino acid sequence of the modified human IgG$_4$ Fc domain is underlined with a dashed line.

FIG. 3 depicts a summary table of study dose escalation schema and corresponding predicted BMS-986090 serum concentration, receptor occupancy (RO), and exposure margin in human.

FIG. 5, comprising FIGS. 5A-5C depict treatment administration for the proposed dose panels of the clinical trial.

DETAILED DESCRIPTION

Figure 2:
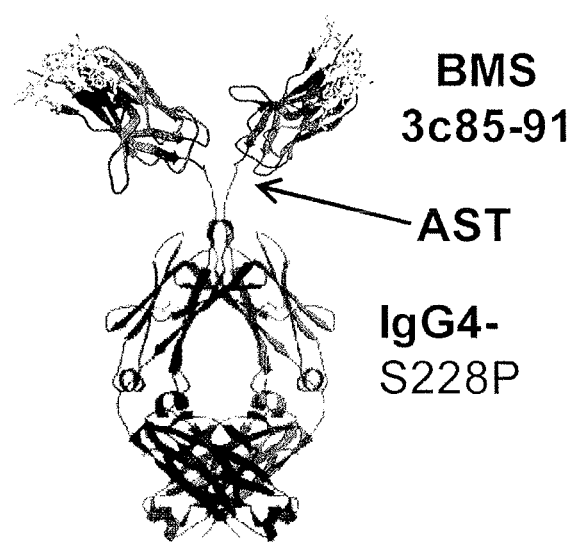
FIG. 2 depicts a schematic representation of a dimer of BMS-986091 wherein the secondary structure of each monomer is depicted in ribbon diagram.

Provided is a method of treating an inflammatory bowel disease (IBD) in a patient in need of such treatment, comprising administering to the patient a therapeutically effective amount of the antibody polypeptide disclosed herein. Also provided is a method where the antibody polypeptide is administered in combination with an immunosuppressive/immunomodulatory and/or anti-inflammatory agent.

Inflammatory bowel disease (IBD) involves chronic inflammation of all or part of the digestive tract. IBD primarily includes ulcerative colitis (UC) and Crohn's disease. IBD further includes Behcet's disease and other forms of colitis, including collagenous colitis, lymphocytic colitis, and diversion colitis. In an embodiment, the IBD treated by the disclosed method is selected from the group consisting of: colitis, Crohn's disease, and Behcet's disease. Colitis encompasses ulcerative colitis, collagenous colitis, lymphocytic colitis, diversion colitis, and indeterminate colitis. In an embodiment, colitis can be selected from the group consisting of: ulcerative colitis, collagenous colitis, lymphocytic colitis, and diversion colitis.

In an embodiment, the IBD is ulcerative colitis. Ulcerative colitis is a chronic, relapsing disease marked by inflammation and ulceration of the colonic mucosa and submucosa. It usually involves the rectum initially but may extend proximally to involve a portion of or the entire colon. In the early stages erythematous and hemorrhagic tissue is observed, progressing to mucosal ulceration with purulent exudate in severe cases. The pattern of ulceration is continuous and may extend the entire length of the colon. Transmural extension of the ulceration can result in perforation of the bowel wall causing ileus and peritonitis. The most common symptoms of UC are rectal bleeding, lower abdominal pain and diarrhea, with periods of remission and exacerbation of symptoms.

The epidemiology of ulcerative colitis varies considerably worldwide. The highest incidence and prevalence rates are in the developed world, but incidence is increasing in developing countries. In a recent systematic review of population based studies, incidence varied from 0.6 to more than 20 cases per 100,000 persons per year in Europe and North America, compared with 0.1 to 6.3 cases per 100,000 person per years in Asia and the Middle East. Peak incidence occurred in the second to fourth decade of life, although a modest rise was also seen in later life. Prevalence has been estimated at 7.6 to 246.0 cases per 100,000 per year.

In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

As used here, the term "about" is understood by persons of ordinary skill in the art and will vary to some extent on the context in which it is used. Generally, about encompasses a range of values that are plus/minus 10% of a referenced value.

It is understood that any and all whole or partial integers between the ranges set forth here are included herein.

1. Antibody Polypeptides

The method is practiced by administering an antibody polypeptide that specifically binds to human CD40. The antibody polypeptides do not exhibit CD40 agonist activity, and the antibody polypeptides are useful in the treatment of diseases involving CD40 activation, such as an inflammatory bowel disease (IBD). The antibody polypeptides specifically bind an epitope of human CD40, which does overlap the Chi220 epitope. The human CD40 epitope specifically bound by an antibody polypeptide useful in the disclosed method comprises at least one CD40 amino acid residue selected from the group consisting of Trp109, Leu121, His122, Ser124, Ser156, Ala157, Phe158, Glu159, and His162 of human CD40 (SEQ ID NO: 3). The antibody polypeptides advantageously do not exhibit CD40 agonist activity. The antibody polypeptides were selected using a primary screen that utilizes cell binding assays and human CD40, followed by one or more rounds of error-prone or degenerate oligonucleotide-directed affinity maturation, providing a genus of antibody polypeptides that specifically bind a single CD40 epitope, as described in co-assigned U.S. Publication No. 2014/0099317, published Apr. 10, 2014, entitled "ANTIBODY POLYPEPTIDES THAT ANTAGONIZE CD40," which is incorporated herein by reference in its entirety. The antibody polypeptides were characterized structurally and functionally, and that data is also described in co-assigned U.S. Publication No. 2014/0099317, published Apr. 10, 2014.

In one aspect of the disclosed method, an antibody polypeptide comprises a variable domain that specifically binds human CD40, where the antibody polypeptide competes with the binding of the domain antibody (dAb) which comprises the amino acid sequence of BMS3h-56-269 (SEQ ID NO: 1) as shown below.

```
BMS3h-56-269
EVQLLESGGGLVQPGGSLRLSCAASGFTFRDYEMWWVRQAPGKGLERVSA

INPQGTRTYYADSVKGRFTISRDNSKNTLYLQMNSLRAEDTAVYYCAKLP

FRFSDRGQGTLVTVSS
```

The amino acid sequence of BMS3h-56-269 is also shown in FIG. 1A, wherein the three complementarity-determining regions are underlined. An exemplary nucleic acid sequence encoding the amino acid sequence of BMS3h-56-269 is SEQ ID NO: 2.

The antibody polypeptides may be domain antibodies containing a single variable domain. The antibody polypeptides also may comprise additional domains, such as an Fc domain.

As used herein, "specific binding" refers to the binding of an antigen by an antibody polypeptide with a dissociation constant ($K_d$) of about 1 µM or lower as measured, for example, by surface plasmon resonance. Suitable assay systems include the BIAcore™ surface plasmon resonance system and BIAcore™ kinetic evaluation software (e.g., version 2.1). The affinity or $K_d$ for a specific binding interaction may be about 500 nM or lower or about 300 nM or lower. In the antibody polypeptide administered in the disclosed method of treating an IBD, the first variable domain optionally has an apparent binding constant of 1 pM to 100 nM (e.g., 1 pM to 10 nM).

1.1. CD40 and CD40 Activities

The method of treating an IBD comprises administering a pharmaceutical composition comprising an antibody polypeptide that binds human CD40. CD40 is also known as B-cell surface antigen CD40, Bp50, CD40L receptor, CDw40, CDW40, MGC9013, p50, TNFRSF5, and Tumor necrosis factor receptor superfamily member 5. Relevant structural information for human CD40 can be found, for example, at UniProt Accession Numbers P25942, Q9BYU0, and Q53GN5. "Human CD40" refers to the CD40 comprising the following amino acid sequence:

```
                                           (SEQ ID NO: 3)
MVRLPLQCVL WGCLLTAVHP EPPTACREKQ YLINSQCCSL

CQPGQKLVSD CTEFTETECL PCGESEFLDT WNRETHCHQH

KYCDPNLGLR VQQKGTSETD TICTCEEGWH CTSEACESCV

LHRSCSPGFG VKQIATGVSD TICEPCPVGF FSNVSSAFEK

CHPWTSCETK DLVVQQAGTN KTDVVCGPQD RLRALVVIPI

IFGILFAILL VLVFIKKVAK KPTNKAPHPK QEPQEINFPD

DLPGSNTAAP VQETLHGCQP VTQEDGKESR ISVQERQ.
```

CD40 also has been sequenced in *Mus musculus*, *Sus scrofa*, *Bos taurus*, *Gallus gallus*, *Canis familiaris*, *Macaca fascicularis* (cynomolgus monkey), *Ovis aries*, *Equus caballus*, and *Rattus norvegicus*.

Binding of the present antibody polypeptides to CD40 antagonizes CD40 activity. "CD40 activities" include, but are not limited to, T cell activation (e.g., induction of T cell proliferation or cytokine secretion), macrophage activation (e.g., the induction of reactive oxygen species and nitric oxide in the macrophage), and B cell activation (e.g., B cell proliferation, antibody isotype switching, or differentiation to plasma cells). CD40 activities can be mediated by interaction with other molecules. "CD40 activities" include the functional interaction between CD40 and the following molecules, which are identified by their Uniprot Accession Number is parentheses:

| | |
|---|---|
| CALR | (P27797); |
| ERP44 | (Q9BS26); |
| FBL | (P22087); |
| POLR2H | (P52434); |
| RFC5 | (P40937); |
| SGK1 | (O00141); |
| SLC30A7 | (Q8NEW0); |
| SLC39A7 | (Q92504); |
| TRAF2 | (Q5T1L5); |
| TRAF3 | (Q13114); |
| TRAF6 | (Q9Y4K3); |
| TXN | (Q5T937); |
| UGGT1 | (Q9NYU2); and |
| USP15 | (Q9Y4E8). |

For example, a CD40 "activity" includes an interaction with TRAF2. CD40/TRAF2 interaction activates NF-κB and JNK. See Davies et al., *Mol. Cell Biol.* 25: 9806-19 (2005). This CD40 activity thus can be determined by CD40-dependent cellular NF-κB and JNK activation, relative to a reference. As used herein, the terms "activate," "activates," and "activated" refer to an increase in a given measurable CD40 activity by at least 10% relative to a reference, for example, at least 10%, 25%, 50%, 75%, or even 100%, or more. A CD40 activity is "antagonized" if the activity is reduced by at least 10%, and in an exemplary embodiment, at least about 20%, 30%, 40%, 50%, 60%, 70%, 80%, 90%, 95%, 97%, or even 100% (i.e., no detectable activity), relative to the absence of the antagonist. For example, an antibody polypeptide may antagonize some or all CD40 activity, while not activating CD40. In one embodiment, the antibody polypeptide does not activate B cell proliferation. In another embodiment, the antibody polypeptide does not activate cytokine secretion by T cells, where the cytokine is at least one cytokine selected from the group consisting of IL-2, IL-6, IL-10, IL-13, TNF-α, IFN-γ.

In the disclosed method, the treatment may produce at least one therapeutic effect measurable by a biomarker selected from the group consisting of: total IgG and IgM; CD40 receptor occupancy; a whole blood gene expression biomarker; plasma soluble CD40L; an ex vivo functional whole blood assay biomarker; plasma D-dimer; serum troponin; plasma prothrombin (fragment 1+2); plasma thrombin anti-thrombin (TAT); prothrombin time (INR); C-reactive protein (CRP); immune cell counts (T, B and NK) (WB); serum cytokines; inflammatory markers; serum immunoglobulin (IgM, IgG, IgA); hemoglobin; hematocrit; complete blood count with differential and biochemistry; total leukocyte count; and differential platelet count 1.2. The CD40 Epitope X-ray crystallography of a complex between human CD40 (SEQ ID NO: 3) and the dAb BMS3h-56-5 was used to reveal an epitope recognized by the antibody polypeptides useful in the present disclosure, as described in detail in Example 10 of co-assigned U.S. Publication No. 2014/0099317, published Apr. 10, 2014, entitled "ANTIBODY POLYPEPTIDES THAT ANTAGONIZE CD40." Structural models of CD40 and BMS3h-56-5 were fitted to electron density data to yield seven models or versions of the CD40/BMS3h-56-5 complex, which come from three crystallographically independent complexes in one crystal form and four crystallographically independent complexes in a second crystal form. The versions have real space correlation coefficients of about 0.92 for main-chain atoms and 0.80 for side-chain atoms. The CD40 molecule has a certain amount of flexibility in the seven versions, but the overall nature of the CD40/BMS3h-56-5 interaction is retained in all versions. The versions differ in the interaction between the CD40 residue Trp109 and BMS3h-56-5 Trp103 (Kabat Numbering). BMS3h-56-5 Trp103 forms an edge-to-face interaction with CD40 Trp109 in one version, while forming a displaced stacking (i.e., face-to-face) interaction in other versions. The shape complementarity statistic, Sc, for the seven versions ranges from 0.70-0.77, which shows a higher degree of shape complementarity than for typical antibody/antigen complexes.

A model of the human CD40/BMS3H-56-5 complex is shown in FIG. 1 of co-assigned U.S. Publication No. 2014/0099317. One BMS3h-56-5 dAb binds to one CD40 molecule in the human CD40/BMS3H-56-5 complex. The BMS3h-56-5 epitope does not overlap the Chi220 Fab' fragment epitope.

The minimal CD40 epitope for BMS3h-56-5 is defined as CD40 residues containing at least one atom in van der Waals or hydrogen-bond contact with a BMS3h-56-5 atom. All versions of the complex define a set of CD40 residues that contact BMS3h-56-5: Trp109, Leu121, His122, Ser124, Ser156, Ala157, Phe158, Glu159, and His162 (with reference to SEQ ID NO: 3), which set is the minimum epitope. CD40 residues that contact BMS3h-56-5 (van der Waals or hydrogen-bond contact) in some versions of the complex are Pro85, Asn86, Leu87, Gly88, Glu106, Glu107, Gly108, His110, Thr112, Cys119, Val120, Gln133, Ile134, Ala135, Thr136, Ser155, and Lys160.

A maximal CD40 epitope is defined as residues containing atoms that are buried by a 1.7 Å probe sphere. Val154 is a buried CD40 residue in all versions. Other CD40 residues buried in some versions are Ser118, Arg123, Thr141, Phe151, Asp153, Cys161, and Pro163.

As used herein, the term "in contact" refers to an interatomic distance whose maximum is determined by an atom type distance dependency as defined by Sheriff et al., *J. Mol. Biol.* 197: 273-296 (1987) and Sheriff, *Immunomethods* 3: 191-196 (1993).

As used herein, the term "buried" refers to a residue that has a least one atom with surface area defined by the program MS (Connolly, *J. Appl. Crystallogr.* 16: 548-558 (1983)), a probe sphere of 1.7 Å, and atom type dependent Van der Waals radii as defined by Sheriff, *Immunomethods* 3: 191-196 (1993).

In summary, the CD40 epitope comprises one or more residues listed in TABLE 1, with reference to the numbering used in SEQ ID NO: 3.

TABLE 1

| CD40 residues contacting BMS3h-56-5: |
|---|
| Trp109, Leu121, His122, Ser124, Ser156, Ala157, Phe158, Glu159, His162 |

BMS3h-56-5 was prepared by a screening and affinity maturation method described in co-assigned U.S. Publication No. 2014/0099317, published Apr. 10, 2014, entitled "ANTIBODY POLYPEPTIDES THAT ANTAGONIZE CD40, using human CD40 as the antigen. It is expected that dAbs created by affinity maturation from a common precursor dAb will bind the same human CD40 epitope. Competition studies described below, for example, indicate that dAbs generated from a common precursor dAb by affinity maturation compete for binding with each other to human CD40. The same competition studies, however, show that the dAbs do not compete with at least the Chi220 or G28-5 antibodies.

1.3. Antibody Polypeptides

The antibody polypeptides comprise a variable domain. In one embodiment, the antibody polypeptides are in the form of a dAb that contains a single variable domain. Antibody polypeptides may be full-length anti-CD40 immunoglobulin molecules comprising two heavy (H) chains and two light (L) chains interconnected by disulfide bonds. In this embodiment, the amino terminal portion of each chain includes a variable domain ($V_L$ or $V_H$) of about 100-110 amino acids primarily responsible for antigen recognition via the complementarity determining regions (CDRs) contained therein. The carboxy-terminal "half" of each heavy chain defines a constant region (Fc) primarily responsible for effector function.

Antibody polypeptides also may be "fragments" comprising a portion of the full-length anti-CD40 immunoglobulin molecule that comprises a variable domain that specifically binds CD40. Thus, the term "antibody polypeptides" includes an antigen-binding heavy chain, light chain, heavy chain-light chain dimer, Fab fragment, F(ab')$_2$ fragment, Fv fragment, single chain Fv (scFv), and dAb, for example. The term "antibody polypeptides" thus includes polypeptides made by recombinant engineering and expression, as well as monoclonal antibodies produced by natural recombination and secretion by hybridoma cell clones.

Light chains are classified as kappa (κ) or lambda (λ), and are characterized by a particular constant region, $C_L$, as known in the art. Heavy chains are classified as γ, μ, α, δ, or Σ, and define the isotype of an antibody as IgG, IgM, IgA, IgD, or IgE, respectively. The heavy chain constant region is comprised of three domains (CH1, CH2, and CH3) for IgG, IgD, and IgA; and four domains (CH1, CH2, CH3, and CH4) for IgM and IgE. Anti-CD40 antibodies may have a heavy chain constant region selected from any of the immunoglobulin classes (IgA, IgD, IgG, IgM, and IgE).

Each light chain variable domain ($V_L$) and heavy chain variable domain ($V_H$) is composed of three CDRs and four framework regions (FRs), arranged from amino-terminus to carboxy-terminus in the following order: FR1, CDR1, FR2, CDR2, FR3, CDR3, FR4. The three CDRs of the light chain may be referred to as "LCDR1, LCDR2, and LCDR3" and the three CDRs of the heavy chain may be referred to as "HCDR1, HCDR2, and HCDR3."

As used herein, the term "Fc domain" refers to the constant region antibody sequences comprising CH2 and CH3 constant domains as delimited according to Kabat et al., *Sequences of Immunological Interest*, 5$^{th}$ ed., U.S. Dept. Health & Human Services, Washington, D.C. (1991). The Fc region may be derived from a human IgG. For instance, the Fc region may be derived from a human IgG1 or a human IgG4 Fc region, for example. A variable domain may be fused to an Fc domain. In this case, the carboxyl terminus of the variable domain (either a $V_L$ or $V_H$ domain, including dAbs) may be linked or fused to the amino terminus of the Fc CH2 domain. Alternatively, the carboxyl terminus of the variable domain may be linked or fused to the amino terminus of a linker amino acid sequence, which itself is fused to the amino terminus of an Fc domain. Alternatively, the carboxyl terminus of the variable domain may be linked or fused to the amino terminus of a CH1 domain, which itself is fused to the Fc CH2 domain. The protein may comprise the hinge region between the CH1 and CH2 domains in whole or in part.

The CDRs contain most of the residues that form specific interactions with the antigen. For example, the variable domain of an antibody polypeptide comprises CDR1, CDR2, and CDR3 regions that have the same amino acid sequence as the CDR1, CDR2, and CDR3 regions of BMS3h-56-269 or that each differ from the CDR1, CDR2, and CDR3 regions by one or two amino acids.

A "domain antibody" (dAb) comprises a single variable ($V_L$ or $V_H$) domain that is capable of specifically and monovalently binding an antigen, such as CD40. For example, a dAb may have a $V_{HH}$ structure, characteristic of a camelid dAb. A "$V_H$ domain" as used herein is meant to include a $V_{HH}$ structure. In another embodiment, the $V_H$ domains of the present invention (including all features and combination of features presented as embodiments herein) are other than $V_{HH}$ domains. dAbs may form homo- or heterodimers in solution. Bivalent anti-CD40 antibodies are believed to exhibit agonist activity because of the ability to cross-link bound CD40 molecules on the cell surface. While not limited by any particular theory, it is believed that monovalent dAbs do not activate CD40, because the dAbs do not cross-link CD40.

As used herein, the term "variable domain" refers to immunoglobulin variable domains defined by Kabat et al., *Sequences of Immunological Interest*, 5$^{th}$ ed., U.S. Dept. Health & Human Services, Washington, D.C. (1991). The numbering and positioning of CDR amino acid residues within the variable domains is in accordance with the well-known Kabat numbering convention. For example, the Kabat numbering for BMS3h-56-269 (SEQ ID NO: 1) is compared in TABLE 2 to the same sequence numbered sequentially. In the Kabat numbering, BMS3h-56-269 has insertion residues 52A, 82A, 82B, 82C, and is missing residue 100.

TABLE 2

```
                                               CDR1
Kabat                    10        20        30        40
50

-  |    -  |    -  |    -  |    -  |
Sequential               10        20        30        40
50

-  |    -  |    -  |    -  |    -  |
BMS3h-56-269     EVQLLESGGGLVQPGGSLRLSCAASGFTFRDYEMWWVRQAPGKGLERVSA
                        CDR2
Kabat                    60        70        80             90
                     A - |    -  |    -  |  ABC  -      |  -
Sequential               60        70        80             90
100

-  |    -  |    -  |    -  |       |
```

TABLE 2-continued

```
BMS3h-56-269    INPQGTRTYYADSVKGRFTISRDNSKNTLYLQMNSLRAEDTAVYYCAKLP

CDR3
Kabat              101       110 113
                    |    -    |   |
Sequential                  110    116
                      -      |    -|
BMS3h-56-269    FRFSDRGQGTLVTVSS              (SEQ ID NO: 1)
```

The term "human," when applied to antibody polypeptides, means that the antibody polypeptide has a sequence, e.g., FR and/or CH domains, derived from a human immunoglobulin. A sequence is "derived from" a human immunoglobulin coding sequence when the sequence is either: (a) isolated from a human individual or from a cell or cell line from a human individual; (b) isolated from a library of cloned human antibody gene sequences or of human antibody variable domain sequences; or (c) diversified by mutation and selection from one or more of the polypeptides above. An "isolated" compound as used herein means that the compound is removed from at least one component with which the compound is naturally associated with in nature.

Antibody polypeptides can be administered to human patients while largely avoiding the anti-antibody immune response often provoked by the administration of antibodies from other species, e.g., mouse. For example, murine antibodies can be "humanized" by grafting murine CDRs onto a human variable domain FR, according to procedures well known in the art. Human antibodies as disclosed herein, however, can be produced without the need for genetic manipulation of a murine antibody sequence.

Variable domains may comprise one or more framework regions (FR) with the same amino acid sequence as a corresponding framework region encoded by a human germline antibody gene segment. For example, a domain antibody may comprise the $V_H$ germline gene segments DP47, DP45, or DP38, the $V_K$ germline gene segment DPK9, the $J_H$ segment JH4b, or the $J_K$ segment $J_K1$.

Changes may be made to antibody polypeptide sequences while retaining the ability to bind CD40 specifically. Specifically, the antibody polypeptides (e.g., a dAb) may comprise a variant variable domain that retains the function of specifically binding the same CD40 epitope as the dAb BMS3h-56-269. That is, the variant variable domain may bind a human CD40 epitope comprising at least one of Trp109, Leu121, His122, Ser124, Ser156, Ala157, Phe158, Glu159, and His162 of SEQ ID NO: 3. In one embodiment, the variant variable domain epitope may comprise Trp109, Leu121, His122, Ser124, Ser156, Ala157, Phe158, Glu159, and His162. Alternatively, the variant variable domain may specifically bind a CD40 epitope comprising CD40 residue Trp109. In yet another embodiment, the variant variable domain may compete with BMS3h-56-269 for specific binding to CD40. Error-prone affinity maturation, as disclosed co-assigned U.S. Publication No. 2014/0099317, published Apr. 10, 2014, provides one exemplary method for making and identifying antibody polypeptides with variant sequences that specifically bind the same CD40 epitope.

For example, a variant variable domain may differ from the variable domain of BMS3h-56-269 by up to 10 amino acids or any integral value between, where the variant variable domain specifically binds CD40. Alternatively, the variant variable domain may have at least 90% sequence identity (e.g., at least 92%, 95%, or 98% sequence identity) relative to the sequence of BMS3h-56-269. Non-identical amino acid residues or amino acids that differ between two sequences may represent amino acid substitutions, additions, or deletions. Residues that differ between two sequences appear as non-identical positions, when the two sequences are aligned by any appropriate amino acid sequence alignment algorithm, such as BLAST.

The information regarding the boundaries of the $V_L$ or $V_H$ domains of heavy and light chain genes may be used to design PCR primers to amplify the variable domain from a cloned heavy or light chain coding sequence encoding an antibody polypeptide known to bind CD40. The amplified variable domain may be inserted into a suitable expression vector, e.g., pHEN-1 (Hoogenboom et al. (1991) *Nucleic Acids Res.* 19:4133-4137) and expressed, either alone or as a fusion with another polypeptide sequence, using techniques well known in the art. Based on the disclosed amino acid and polynucleotide sequences, the fusion protein can be produced and purified using only ordinary skill in any suitable mammalian host cell line, such as CHO, 293, COS, NSO, and the like, followed by purification using one or a combination of methods, including protein A affinity chromatography, ion exchange, reverse phase techniques, or the like.

In one aspect, the antibody polypeptide is a fusion antibody polypeptide comprising a first variable domain that specifically binds human CD40 comprising the amino acid sequence of SEQ ID NO: 3, and a second domain comprising an Fc domain. In one embodiment of the disclosed method, the first variable domain comprises the amino acid sequence of BMS3h-56-269 (SEQ ID NO: 1) or differs from the amino acid sequence of BMS3h-56-269 (SEQ ID NO: 1) by up to 5 amino acids. Exemplary Fc domains include human IgG domains. Exemplary human IgG Fc domains include IgG4 Fc domain and IgG1 Fc domain. In an embodiment of the disclosed method, the Fc domain comprises an amino acid sequence selected from SEQ ID NO: 4 and SEQ ID NO: 6. In an embodiment of the disclosed method, the antibody polypeptide comprises a variable domain wherein the amino acid sequence of the variable domain comprises BMS3h-56-269 (SEQ ID NO: 1) or differs from the amino acid sequence of BMS3h-56-269 (SEQ ID NO: 1) by up to 5 amino acids and (2) a human Fc domain selected from SEQ ID NO: 4 and SEQ ID NO: 6. In an embodiment of the disclosed method, the antibody polypeptide comprises or consists of BMS3h-56-269-IgG$_4$ Fc fusion polypeptide (SEQ ID NO: 5).

In one embodiment, antibody polypeptides of a fusion antibody polypeptide may be linked by an "amino acid linker" or "linker." For example, a dAb may be fused to the N-terminus of an amino acid linker, and an Fc domain may be fused to the C-terminus of the linker. Although amino acid linkers can be any length and consist of any combination of amino acids, the linker length may be relatively short (e.g., five or fewer amino acids) to reduce interactions between the linked domains. The amino acid composition of the linker also may be adjusted to reduce the number of amino acids with bulky side chains or amino acids likely to introduce secondary structure. Suitable amino acid linkers include, but are not limited to, those up to 3, 4, 5, 6, 7, 10, 15, 20, or 25 amino acids in length. Representative amino acid linker sequences include GGGGS (SEQ ID NO: 8), and linker comprising 2, 3, 4, or 5 copies of GGGGS (SEQ ID NOs: 9-12, respectively). Table 3 lists suitable linker sequences for use in the present disclosure.

TABLE 3

Representative Linker Sequences

| | |
|---|---|
| GGGGS | SEQ ID NO: 8 |
| (GGGGS)$_2$ | SEQ ID NO: 9 |
| (GGGGS)$_3$ | SEQ ID NO: 10 |
| (GGGGS)4 | SEQ ID NO: 11 |
| (GGGGS)$_5$ | SEQ ID NO: 12 |
| AST | SEQ ID NO: 13 |
| TVAAPS | SEQ ID NO: 14 |
| TVA | SEQ ID NO: 15 |
| ASTSGPS | SEQ ID NO: 16 |

In an embodiment of the disclosed method, the first variable domain comprises the amino acid sequence of BMS3h-56-269 (SEQ ID NO: 1) or differs from the amino acid sequence of BMS3h-56-269 (SEQ ID NO: 1) by up to 5 amino acids fused to a linker that is fused to a human Fc domain. In an embodiment of the disclosed method, the linker is selected from any of the linker in Table 3. In an embodiment, the linker is AST (SEQ ID NO: 13). In an embodiment of the disclosed method, the antibody polypeptide comprises a variable domain wherein the amino acid sequence of the variable domain comprises BMS3h-56-269 (SEQ ID NO: 1) or differs from the amino acid sequence of BMS3h-56-269 (SEQ ID NO: 1) by up to 5 amino acids, a linker comprising SEQ ID NO: 13 or SEQ ID NO: 8, and a human Fc domain selected from SEQ ID NO: 4 and SEQ ID NO: 6. In an embodiment of the disclosed method, the antibody polypeptide comprises a variable domain wherein the amino acid sequence of the variable domain comprises BMS3h-56-269 (SEQ ID NO: 1), a linker comprising AST (SEQ ID NO: 13), and a human Fc domain comprising the amino acid sequence of SEQ ID NO: 4.

In an embodiment of the disclosed method of treating an IBD by administering an antibody polypeptide, the amino acid sequence of the first variable domain comprises (a) a CDR1 region which differs from the CDR1 region of BMS3h-56-269 (amino acids 31-35 of SEQ ID NO: 1) by up to two amino acids, (b) a CDR2 region which differs from the CDR2 region of BMS3h-56-269 (amino acids 50-66 of SEQ ID NO: 1) by up to two amino acids, (c) a CDR3 region which differs from the CDR3 region of BMS3h-56-269 (amino acids 99-105 SEQ 1D NO: 1) by up to two amino acids. In another embodiment of the disclosed method of treating an IBD by administering an antibody polypeptide, the amino acid sequence of the first variable domain comprises (a) a CDR1 region which differs from the CDR1 region of BMS3h-56-269 (amino acids 31-35 of SEQ ID NO: 1) by up to two amino acids, (b) a CDR2 region which differs from the CDR2 region of BMS3h-56-269 (amino acids 50-66 of SEQ ID NO: 1) by up to two amino acids, (c) a CDR3 region which differs from the CDR3 region of BMS3h-56-269 (amino acids 99-105 SEQ ID NO: 1) by up to two amino acids, (d) a FR1 region which differs from the FR1 region of BMS3h-56-269 (amino acids 1-30 of SEQ ID NO: 1) by up to two amino acids, (e) a FR2 region which differs from the FR2 region of BMS3h-56-269 (amino acids 36-49 of SEQ ID NO: 1) by up to two amino acids, (f) a FR3 region which differs from the FR3 region of BMS3h-56-269 (amino acids 67-98 of SEQ ID NO: 1) by up to two amino acids, and (g) a FR4 region which differs from the FR4 region of BMS311-56-269 (amino acids 106-116 of SEQ ID NO: 1) by up to two amino acids. Exemplary consensus amino acid sequences for CDR1, CDR2, CDR3, FR1, FR2, FR3 and FR4 are disclosed in SEQ ID NOS: 17-23, respectively.

In another embodiment, an antibody polypeptide may be formatted to increase its in vivo half-life by PEGylation. In an embodiment of the disclosed method of treating an IBD by administering an antibody polypeptide, the antibody polyptide is linked to one or more PEG polymers. In one embodiment, the PEG is covalently linked. In another embodiment, the PEG is linked to the antibody polypeptide at a cysteine or lysine residue. In yet another embodiment, the PEG-linked antibody polypeptide has a hydrodynamic size of at least 24 kD. In yet another embodiment, the total PEG size is from 20 to 60 kD, inclusive. In yet another embodiment, the PEG-linked domain antibody has a hydrodynamic size of at least 200 kD.

PEGylation can be achieved using several PEG attachment moieties including, but not limited to N-hydroxylsuccinimide active ester, succinimidyl propionate, maleimide, vinyl sulfone, or thiol. A PEG polymer can be linked to an antibody polypeptide at either a predetermined position, or can be randomly linked to the domain antibody molecule. PEGylation can also be mediated through a peptide linker attached to a domain antibody. That is, the PEG moiety can be attached to a peptide linker fused to an antibody polypeptide, where the linker provides the site (e.g., a free cysteine or lysine) for PEG attachment. Methods of PEGylating antibodies are well known in the art, as disclosed in Chapman, et al., "PEGylated antibodies and antibody fragments for improved therapy: a review," *Adv. Drug Deliv. Rev.* 54(4):531-45 (2002), for example.

Antibody polypeptides also may be designed to form a dimer, trimer, tetramer, or other multimer. Antibody polypeptides, e.g., dAbs, can be linked to form a multimer by several methods known in the art, including, but not limited to, expression of monomers as a fusion protein, linkage of two or more monomers via a peptide linker between monomers, or by chemically joining monomers after translation, either to each other directly, or through a linker by disulfide bonds, or by linkage to a di-, tri- or multivalent linking moiety (e.g., a multi-arm PEG). In one embodiment, the multimer can bind a single molecule of CD40.

2. Pharmaceutical Compositions and Methods of Treatment

The disclosed method of treating an IBD in a human patient comprises administering an antibody polypeptide in a therapeutically-effective amount to the patient. Antagonizing CD40-mediated T cell activation could inhibit undesired T cell responses occurring during autoimmunity, for example in inflammatory bowel disease (IBD). Inhibiting CD40-mediated T cell activation could moderate the progression and/or severity of an IBD.

As used herein, a "patient" means an animal, e.g. mammal, including humans.

"Treatment" or "treat" or "treating" refers to the process involving alleviating the progression or severity of a symptom, disorder, condition, or disease. An "autoimmune disease" refers to any disease associated with the development of an autoimmune reaction in an individual, including a cellular and/or a humoral immune reaction. An example of an autoimmune disease is inflammatory bowel disease, including, but not limited to ulcerative colitis and Crohn's disease.

The antibody polypeptide may be administered alone or in combination therapy, (i.e., simultaneously or sequentially) with an immunosuppressive/immunomodulatory and/or anti-inflammatory agent. Simultaneous administration comprises administering an antibody polypeptide and an immunosuppressive/immunomodulatory and/or anti-inflammatory agent, either in a single composition, or as separate compositions administered at substantially the same time. Different IBDs can require use of specific auxiliary compounds useful for treating an IBD such as ulcerative colitis, which can be determined on a patient-to-patient basis. For example, the antibody polypeptide may be administered in combination with a conventional therapeutic agent for an IBD. Exemplary therapeutic agents for ulcerative colitis, for instance, include sulfasalazine and medications that contain 5-aminosalicylate acid (5-ASA) such as sulfasalazine, mesalamine, olsalazine, and balsalazide, given orally, rectally (by means of suppository or enema) or both. Other suitable therapeutic agents, such as oral glucocorticoids and immunosuppressive agents (azathioprine or 6-mercaptopurine), are known in the art.

The antibody polypeptide may also be administered as a pharmaceutically composition comprising a therapeutically-effective amount of one or more antibody polypeptides and optionally a pharmaceutically acceptable carrier. Pharmaceutically acceptable carriers include, for example, water, saline, phosphate buffered saline, dextrose, glycerol, ethanol and the like, as well as combinations thereof. Pharmaceutically acceptable carriers can further comprise minor amounts of auxiliary substances, such as wetting or emulsifying agents, preservatives, or buffers that enhance the shelf-life or effectiveness of the fusion protein. The compositions can be formulated to provide quick, sustained, or delayed release of the active ingredient(s) after administration. Suitable pharmaceutical compositions and processes for preparing them are well known in the art. See, e.g., Remington, THE SCIENCE AND PRACTICE OF PHARMACY, A. Gennaro, et al., eds., 21st ed., Mack Publishing Co. (2005).

The pharmaceutical composition comprising the antibody polypeptide further may comprise an immunosuppressive/immunomodulatory and/or anti-inflammatory agent. A method of treating an autoimmune disease in a patient in need of such treatment may comprise administering to the patient a therapeutically effective amount of the pharmaceutical composition.

Any suitable method or route can be used to administer the antibody polypeptide or the pharmaceutical composition. Routes of administration include, for example, oral, intravenous, intraperitoneal, subcutaneous, or intramuscular administration. In an embodiment, the route of administration is intravenous or subcutaneous. The antibody polypeptide can be administered daily, weekly, biweekly, every 2-3 weeks, every 3-4 weeks, or monthly.

A therapeutically effective dose of administered antibody polypeptide(s) depends on numerous factors, including, for example, the type and severity of the IBD being treated, the use of combination therapy, the route of administration of the antibody polypeptide(s) or pharmaceutical composition, and the weight of the patient. A non-limiting range for a therapeutically effective amount of an antibody polypeptide is 0.1-20 mg/kg, and in an aspect, 1-10 mg/kg, relative to the body weight of the patient. It is understood that any and all whole or partial integers between the ranges set forth here are included herein. A non-limiting range for a therapeutically effective amount of an antibody polypeptide, such as an antibody polypeptide comprising (1) a variable domain wherein the amino acid sequence of the variable domain comprises BMS3h-56-269 (SEQ ID NO: 1) or differs from the amino acid sequence of BMS3h-56-269 (SEQ ID NO: 1) by up to 5 amino acids and (2) a human Fc domain, is from 0.5 mg subcutaneously (SC) to 750 mg intravenously (IV) to patients; for example, 0.5 to 300 milligrams (mg) SC; or 100 mg to 750 mg IV of antibody polypeptide. Exemplary ranges for SC doses include, but are not limited to, 0.5 mg to 3 mg to 10 mg SC; 30 mg to 100 mg to 150 mg SC; and 100 mg to 150 mg to 300 mg SC of antibody polypeptide. SC doses include, but are not limited to, 0.5 mg, 1 mg, 2 mg, 3 mg, 4 mg, 5 mg, 6 mg, 7 mg, 8 mg, 9 mg, 10 mg, 15 mg, 20 mg, 25 mg 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, and 300 mg of antibody polypeptide. Exemplary SC doses include, but are not limited to, 0.5 mg, 3 mg, 10 mg, 30 mg, 100 mg, 150 mg and 300 mg of antibody polypeptide. Exemplary IV doses include, but are not limited to, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 320 mg, 340 mg, 360 mg, 380 mg, 400 mg, 420 mg, 440 mg, 460 mg, 480 mg, 500 mg, 520 mg, 540 mg, 560 mg, 580 mg, 600 mg, 620 mg, 640 mg, 660 mg, 680 mg, 700 mg, 710 mg, 720 mg, 730 mg, 740 mg, and 750 mg of antibody polypeptide. Exemplary IV doses include, but are not limited to, 100 mg, 200 mg, 250 mg, 300 mg, 400 mg, 500 mg, 600 mg, 700 mg, and 750 mg of antibody polypeptide. The dose of antibody polypeptide(s) can be further guided by the amount of antibody polypeptide(s) required for CD40 antagonism in in vitro and/or in vivo models of disease states. Representative models are described below and in the examples.

Patients treated according to the methods disclosed herein experience improvement in at least one sign of the IBD. Primary Biomarkers of domain antibody efficacy includes total IgG and IgM, CD40 receptor occupancy, whole blood gene expression, plasma soluble CD40L, ex vivo functional whole blood assays. Domain antibody safety biomarkers include plasma D-dimer, serum troponin, plasma prothrombin (fragment 1+2), plasma thrombin anti-thrombin (TAT), prothrombin time (INR), C-reactive protein (CRP), immune cell counts (T, B and NK) (WB), serum cytokines and inflammatory markers, and serum immunoglobulin (IgM, IgG, IgA). Hematological biomarkers include hemoglobin, hematocrit, complete blood count with differential and biochemistry, total leukocyte count, including differential platelet count.

2.1. Inflammatory Bowel Disease (IBD) In Vitro and In Vivo Models

The ability of antibody polypeptides of the disclosure to antagonize CD40 can be tested in one of several available in vitro or in vivo model systems. Appropriate animal and cell model systems are described below. Further cell assay systems are described in the examples.

IBD is a multifactorial immune disorder of uncertain etiology. Several mouse models of mucosal inflammation that resemble IBD have provided insight into the mechanisms governing both normal and pathological mucosal immune function. IBD models include using the mucosal immunity and inflammation system of De Winter et al., *Am. J. Physiol.* 276: G1317-1321 (1999). In one aspect, the injection into immunodeficient mice of a subset of CD4(+) T lymphocytes, the CD4(+)CD45RBhigh cells, leads to inflammation of the intestine. Pathogenesis is due in part to the secretion of proinflammatory cytokines. The induction of colitis can be prevented by co-transfer of another CD4(+) subpopulation, the CD4(+)CD45RBlow T cells. This population behaves analogously to the CD4(+)CD45RBhigh population in terms of the acquisition of activation markers and homing to the host intestine. However, their lymphokine profile when activated is different, and anti-inflammatory cytokines secreted and/or induced by CD4(+)CD45RBlow T cells prevent colitis. De Winter et al. provide a description of the adoptive transfer model and the factors that promote and prevent colitis pathogenesis.

3. Kits

A kit useful for treating an inflammatory bowel disease (IBD) in a human patient is provided. In an embodiment, the kit comprise (a) a dose of an antibody polypeptide comprising BMS3h-56-269-IgG$_4$ Fc fusion polypeptide (SEQ ID NO: 5), and (b) instructional material for using the antibody polypeptide in the method of treating an inflammatory bowel disease (IBD) in a human patient as disclosed herein.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The dose may be 0.5 to 300 milligrams (mg) SC; or 100 mg to 750 mg IV of antibody polypeptide. Exemplary ranges for SC doses include, but are not limited to, 0.5 mg to 3 mg to 10 mg SC; 30 mg to 100 mg to 150 mg SC; and 100 mg to 150 mg to 300 mg SC of antibody polypeptide. Exemplary IV doses include, but are not limited to, 100 mg, 200 mg, 250 mg, 300 mg, 400 mg, 500 mg, 500 mg, 700 mg, and 750 mg of antibody polypeptide. Other exemplary doses are disclosed elsewhere herein. Optionally, the dose may be in the form of a pharmaceutical composition comprising the antibody polypeptide and a pharmaceutically acceptable carrier.

EXAMPLES

Example 1

Monkey Toxicity Studies

There is no significant crossreactivity of BMS3h-56-269-IgG$_4$ Fc fusion polypeptide (SEQ ID NO: 5) to CD40 in any traditional nonclinical toxicology species. Therefore, a surrogate domain antibody BMS-986091 with crossreactivity to cynomolgus monkey CD40 receptors was developed for use in nonclinical pharmacology and toxicology assessments. The non-human primate was selected as the toxicology species because BMS-986091 binds to cynomolgus monkey CD40 and is pharmacologically active in monkeys, whereas it does not crossreact with the rodent receptors.

The preparation of surrogate domain antibody BMS-986091 is described in co-assigned U.S. Publication No. 2014/009931. BMS-986091 is a $V_H$ domain antibody (dAb) fragment (BMS3c85-91) fused by an AST linker to a human IgG4 hinge and Fc domain containing an S228P mutation (numbering with respect to entire sequence of BMS-986091). The structure and functional characterization of BMS3c85-91 are also described in co-assigned U.S. Publication No. 2014/009931. The dAb-Fc fusion protein is a dimer of molecular weight 78,043 daltons with each polypeptide chain consisting of 350 amino acids.

FIG. 2 depicts a schematic representation of a dimer of BMS-986091; the secondary structure of each monomer is depicted in ribbon diagram. The dAb domains bind specifically to cynomolgus monkey CD40.

The specificity of BMS-986090 or BMS-986091 for human and non-human primate CD40 proteins, as well as the kinetics and affinity of binding were determined using surface plasmon resonance (SPR). SPR analysis of BMS-986090 or BMS-986091 binding to mutant CD40 proteins, together with of the X-ray crystal structure of human CD40 bound to the human-specific dAb fragment, were used to demonstrate that BMS-986090 and BMS-986091 bind to the homologous epitope (including amino acids 109 and 121) on human CD40 and cynomolgus CD40 respectively. SPR studies demonstrated that BMS-986090 and BMS-986091 have comparable binding affinities for their respective CD40 target proteins. In addition, SPR studies demonstrated that BMS-986090 and BMS-986091 have comparable binding affinities for Fc gamma receptos and human neonatal Fc receptor FcRn. In vitro, BMS-986091 showed similar potency in cynomolgus mixed lymphocyte reaction (MLR) assays compared to the potency of BMS3h-56-269-IgG$_4$ Fc fusion polypeptide in human MLR assays. These data support that BMS-986091 is a suitable surrogate molecule for use in preclinical toxicology studies to suppor the clinical development of BMS-986090.

In previous studies, monkeys receiving CD40 antagonist antibodies (not BMS-986091) at repeated doses up to 100 mg/kg given once weekly, toxicities were limited to target-associated germinal center depletion in lymphoid organs with associated pharmacologic effects and profound Fc-effector associated B-cell depletion occurring shortly after a single dose. The Fc-effector associated B-cell depletion has been engineered out of BMS-986091 and BMS3h-56-269-IgG$_4$ Fc fusion polypeptide via the use of a modified IgG4 Fc fragment as evidenced by a lack of overt, marked B-cell depletion in the single- and repeat-dose dose monkey study.

Completed nonclinical toxicology studies with BMS-986091 include: (1) a single dose pharmacokinetic/pharmacodynamics (PK/PD) study in cynomolgus monkeys; (2) a 3-month SC/IV toxicity study in cynomolgus monkeys with a 3-month recovery period; (3) a tissue binding study evaluating crossreactivity of BMS3h-56-269-IgG$_4$ Fc fusion polypeptide (SEQ ID NO: 5) in human tissues and BMS-986091 in cynomolgus monkey tissues; and (4) an in vitro lymphocyte proliferation and cytokine release study.

Single Dose Pharmacokinetic/Pharmacodynamic (PK/PD) Study in Cynomolgus Monkeys

The PK and PD of BMS-986091 (BMS-986090 monkey surrogate) was evaluated in a single-dose PK/PD and tolerability study in cynomolgus monkeys (DN12013). BMS-986091 was administered subcutaneously at doses of 0 (vehicle), 0.5, 5, or 50 mg/kg and intravenously at a dose of 5 mg/kg to the monkeys (N=2/sex/group). At approximately 24 h after dosing, all monkeys were immunized intramuscularly with 10 mg of keyhole limpet hemocyanin (KLH) to assess the inhibitory effect of BMS-986091 on T-cell dependent antibody response (TDAR) to KLH.

TABLE 4

Single-Dose Pharmacokinetic Parameters
(Mean ± SD) from Cynomolgus Monkeys

| | Route | Dose (mg/kg) | Cmax (µM) | Tmax (h) | AUC(INF) (µM*h) | T-HALF (h) |
|---|---|---|---|---|---|---|
| BMS-986091 | IV | 5 (N = 4) | — | — | 95 ± 10 | 58 ± 2 |
| | SC | 0.5 (N = 4) | 0.009 ± 0.004 | 48 ± 20 | 1.1 ± 0.2 | 35 ± 11 |
| | | 5 (N = 4) | 0.31 ± 0.04 | 30 ± 12 | 77 ± 50 | 48 ± 9 |
| | | 50 (N = 4) | 3.3 ± 0.4 | 24 ± 0 | 946 ± 165 | 232 ± 43 |
| BMS-986090 | IV | 20 (N = 2) | — | — | 696 | 277 |

BMS-986091 exhibited a more than dose-proportional increase in exposure at 0.5 and 50 mg/kg SC doses and a dose-dependent terminal T-HALF, which are characteristic of a saturable clearance mechanism resulting from target-mediated drug disposition (TMDD). See Table 4. After IV administration (5 mg/kg), the plasma concentration vs. time profile of BMS-986091 exhibited an initial distribution phase followed by a mono-exponential decline out to 504 h. Afterwards, the decrease of drug concentration was accelerated due to TMDD, resulting in a short terminal T-HALF of 58 h (2.5 d After the SC administration, the terminal T-HALF were 35 and 48 h at 0.5 and 5 mg/kg, respectively, but was extended to 232 h (10 d) at 50 mg/kg. At 5 mg/kg, the SC bioavailability was estimated to be 81%.

The pharmacokinetics of BMS-986090, the dAb-IgG4 Fc fusion protein targeting human CD40, was also evaluated in cynomolgus monkeys after IV administration at 20 mg/kg. The CLT, Vss and terminal T-HALF were estimated to be 0.36 mL/h/kg, 0.11 L/kg and 277 h, respectively. Because BMS-986090 does not cross-react with monkey CD40 receptors, the lower clearance and longer T-HALF (versus BMS-986091 following a 5 mg/kg IV dose) is consistent with the lack of TMDD.

3-Month SC/IV Toxicity Study in Cynomolgus Monkeys with a 3-Month Recovery Period In the 3-month toxicity study in monkeys at weekly SC doses of 10, 30, or 100 mg/kg or 100 mg/kg IV, BMS-986091 was clinically well tolerated at all doses with effects consistent with the pharmacology of BMS-986091. BMS-986091 doses of ≥10 mg/kg/week (mean AUC (0-168h) 18,300 µg·h/mL) resulted in profound inhibition of the T cell dependent antibody response (TDAR) to KLH (93-100%) following keyhole limpet hemocyanin (KLH) immunization at Week 8. The inhibition of TDAR is consistent with the mechanism of action of this compound.

Additional BMS-986091-related changes at all doses included: (1) decreases in individual globulin values (up to 0.62× pretest) which contributed to small decreases in total protein and increases in albumin to globulin ratio and showed recovery at the end of the recovery phase, and (2) at end-of-dose necropsy, mild to moderate decrease in germinal centers in the axillary, mandibular, and mesenteric lymph nodes and the spleen. These changes were reversible in a rebound-like fashion following the 3-month post-dose period, with minimally increased lymphocytes/germinal centers in axillary, mandibular, and mesenteric lymph nodes, and at ≥30 mg/kg/dose, increased absolute and relative to body and brain spleen weights (males only at 100 mg/kg/dose SQ), grossly enlarged spleens in several monkeys, and a minimal to mild increase in lymphocytes/germinal centers in the splenic white pulp. These findings most likely represented a rebound in B-lymphocyte trafficking/activation/maturation in lymphoid tissues following pharmacologically-mediated CD40 lymphoid suppression.

Additional BMS-986091-related changes at ≥30 mg/kg/week (mean AUC (0-168h) 44,900 µg·h/mL) were limited to reversible decreases in serum IgG levels (0.18×-0.51× group mean pretest) at Weeks 6 and 12; and at 100 mg/kg/week (SC or IV, AUC (0-168h)≥122,000 µg·h/mL), reversible decreases in B lymphocyte absolutes counts (up to 0.66×) in males and females when compared to the pre-dosing and control group values. This is consistent with published reports showing that the level of CD40L (CD154) binding to CD40 on B-lymphocytes can directly influence the evolution/maturation of B cell populations. Furthermore, proliferation, global expansion of CD19+ B-cells and emergence of CD38++ CD138+ B-cells, as well as immunoglobulin G (IgG) and IgM secretion, were affected by the level of exposure of B lymphocytes to CD154. Other investigations support a role for CD154-CD40 interactions in the control of murine B cell hematopoiesis.

Tissue Binding Study Evaluating Crossreactivity of BMS3h-56-269-IgG$_4$ Fe Fusion Polypeptide (SEQ ID NO: 5) in Human Tissues and BMS-986091 in Cynomolgus Monkey Tissues No unexpected binding of BMS3h-56-269-IgG$_4$ Fe fusion polypeptide occurred in a comprehensive panel of human tissues. BMS-986091 had a similar tissue crossreactivity profile in cynomolgus monkey tissues as compared to the binding of BMS-986090 in human tissues.

In Vitro Lymphocyte Proliferation and Cytokine Release Study

BMS-986090 (BMS3h-56-269-IgG$_4$ Fc fusion polypeptide) did not possess substantial PBMC stimulatory activities in an in vitro cytokine release assay, as measured by cell surface expression of T-cell activation antigens (CD25/CD69), lymphocyte proliferation, or cytokine release. BMS-986090 did not induce CD86 expression on human B cells in vitro at concentrations up to 100 µg/mL, indicating that BMS-986090 does not lead to B-cell activation at concentrations well above 100% receptor occupancy (approximately 1 µg/mL). BMS-986090 did not result in induction of cytokine release from human PBMC in vitro (IL-1β, IL-2, IL-5, IL-6, IL-8, IL-10, IL-12(p70), and/or TNF-α) at concentrations up to 10 µg/mL or from isolated human B cells and monocytes (T-cell-depleted PBMCs) or isolated immature dendritic cells at higher concentrations up to 32 µg/mL. Using human PBMC, BMS-986090 at concentrations 32 µg/mL resulted in minimal to mild, but significant release of IL-6, IL-8, IL-12(p70), TNF-α, and IFN-γ, relative to media control. An increase in IL-6, TNFα and IFNγ was not seen with BMS-986090 in T cell-depleted PBMCs at 100 µg/ml, but there was a modest, but significant increase in IL-8. The pattern and low level of cytokine production from PBMC observed with BMS-986090 at concentrations ≥32 µg/mL (ie, well above (>30-fold) 100% receptor occupancy of approximately 1 µg/mL) is consistent with a low level of differential cytokine induction observed for several marketed immunosuppressive antibodies that were screened using an in vitro whole blood cytokine release assay, which were not associated with cytokine storm in vivo, and clearly differentiated from anti-CD28 agonists (i.e., TGN-1412).

Systemic exposures (mean combined gender steady state Cmax and/or AUC values) and corresponding findings at the no observed adverse effect dose (NOAEL) of BMS-986091 tested in the pivotal 3 month (SC/IV weekly) nonclinical toxicity study were compared to the projected systemic exposure of BMS3h-56-269-IgG$_4$ Fc fusion polypeptide (BMS-986090) at the starting SC (0.5 mg) and maximum IV (750 mg) clinical doses assuming a steady dosing interval of every 2 weeks and presented in FIG. 3). The BMS3h-56-269-IgG$_4$ Fc fusion polypeptide exposure (AUC) at the proposed starting IV dose in Study IM142003 based on MABEL (0.5 mg, SC) is projected to be approximately 2,218,182 fold below that of the NOAEL (100 mg/kg/week, IV) exposure of BMS-986091 tested in the 3 month study in monkeys. The BMS3h-56-269-IgG$_4$ Fc fusion polypeptide exposure at the highest proposed dose for Study IM142003 (750 mg, IV) is projected to be approximately 9.5-fold below that of the BMS-986091 NOAEL exposure in the 3 month study in monkeys. All findings in the 3-month monkey study were consistent with the immunosuppressive pharmacology of BMS-986091 (i.e. suppression of TDAR, decreases in lymphoid organ germinal centers, decreases in B cells and immunoglobulins).

Example 2

Clinical Trial Protocol

The clinical trial protocol entitled "Clinical Protocol IM142003 Double-Blinded, Randomized, Placebo-Controlled, Single Ascending Dose and Multiple Dose Study to Evaluate the Safety, Tolerability, Pharmacokinetics and Pharmacodynamics of BMS-986090 (anti-CD40 dAb) in Healthy Subjects" describes in detail a clinical trial protocol. The protocol is excerpted below.

The proposed early clinical development program for BMS-986090 consists of a Phase 1, FIH, study in healthy subjects, followed by a Phase 2, proof of concept (POC) study in subjects with ulcerative colitis (UC). The focus of the Phase 1 study is to establish the safety, tolerability and pharmacokinetics (PK) of BMS-986090 in healthy subjects. The second goal is to establish an efficacious dose range for studies in subjects with UC in Phase 2, applying results from pharmacodynamic (PD) and proof of mechanism (POM) biomarker assessments.

Phase 1
Dose Range Selection

This first-in-human study of BMS-986090 (SEQ ID NO: 5) is a double blind, placebo controlled, and ascending single dose and multiple dose study in healthy subjects. The selection of the dose range is based on the preclinical pharmacokinetic and pharmacodynamic studies as well as single and repeat-dose toxicology studies in animal species.

Six dose levels ranging from 0.5 mg up to 300 mg (0.5, 3, 10, 30, 100, and 300 mg) is administered via SC injection and two dose levels (100 mg and 750 mg) are administered IV via infusion with the following objectives: 1) span a wide range for target engagement (RO); 2) explore exposure/dose response of inhibitory effect of BMS-986090 on KLH induced IgG response following a single SC with adaptive design; 3) understand the safety profile up to 750 mg IV; 4) estimate the absolute bioavailability for BMS-986090 following SC administration; 5) characterize the pharmacokinetics of BMS-986090 under the conditions of target-mediated drug disposition (TMDD) in human. The multiple dose arm (150 mg SC weekly doses for 4 weeks) will provide safety experience at the maximum anticipated exposure levels in the target patient population.

The starting dose was calculated using the Minimal Anticipated Biological Effect Level (MABEL) approach. The exposure (AUC) at the proposed starting dose of 0.5 mg (<10% RO) as SC administration is projected to be approximately 2,218,182 fold below the NOAEL (IV 100 mg/kg/week) exposures tested in the 3 month study in monkeys. The second and third proposed doses (3 mg and 10 mg) are selected to provide predicted RO of 49.8% and 90.3% at Cmax, which allows a gradient increment of RO to mitigate the risk of potential cytokine release associated with targeting CD40 receptor. Additionally, for the first three doses, the receptor occupancy at 1 week and 2 weeks post-dose are expected to drop considerably low, with a range of <2% and <0.2% respectively. The 100 mg IV dose is selected for the purpose of calculating absolute bioavailability of SC formulation of BMS-986090. Panel 6 (100 mg IV) and Panel 7 (300 mg SC) are dosed in parallel. See FIG. 4. The highest proposed dose (750 mg, IV) is selected based on the assessment of safety exposure margins of the human projected efficacious dose 300 mg SC. The exposure at the highest proposed dose for the FIH study (750 mg, IV) is projected to be approximately 9.5-fold below that of the NOAEL (IV 100 mg/kg/week) exposures tested in the 3 month toxicology study in monkeys. The projected efficacious dose in human (300 mg SC) of BMS-986090 provides approximately 42-fold exposure margin relative to the AUC at the NOAEL dose (IV 100 mg/kg/week) in the 3 month monkey toxicology study.

Overall, the proposed doses for this study will span the anticipated efficacious dose range projected for meaningful PD effects and are considered to be within an appropriate safety exposure margin indicated by the nonclinical toxicology results. Dose escalation decisions for the study will depend on a thorough evaluation of the safety and tolerability data for each dose panel (including reported AEs, findings from physical examinations, clinical laboratory results, vital signs, ECGs and safety biomarkers) of the doses up to and including the preceding dose group. In addition, the doses from 6th dose level might be adjusted based on interim analyses using data from 1st five dose levels but will remain within the specified range above.

Selection of Dose Panels Subject to KLH-Immunization

The effect of the BMS-986090 on T cell-dependent antibody response is evaluated by measuring the percent inhibition of immunoglobulin (Ig) titers in KLH-immunized NHVs. Two additional dose levels (30 mg and 100 mg) were selected besides the projected efficacious dose (300 mg) to explore the potential possibility of an exposure/dose response of KLH. The 300 mg SC is expected to provide significant KLH suppression, while the 100 mg and 30 mg are expected to provide less and minimal KLH suppression. The actual KLH dose might be adjusted and additional KLH dose panel might be added based on the interim analyses. KLH is administered at a dose of 1.0 mg subcutaneously on Day 1 for all of the subjects at 30 mg, 100 mg and 300 mg SC dose levels. BMS-986090 at 30 mg, 100 mg, and 300 mg or its placebo is administered SC on Day 1. Both total and KLH-specific immunoglobulin titers are measured pre BMS-986090 dose on Day 1, and on Day 8, Day 15, Day 22 and Day 29 to monitor the inhibition of the KLH-specific antibody responses. If BMS-986090 has the same magnitude of inhibition in human as in monkeys, a similar sustainable inhibition of KLH-induced IgG response could be reached with a single dose.

Study Design and Duration

Twelve (12), healthy subjects are assigned to the SC single dose panels (0.5 mg SC, 3 mg SC, 10 mg SC), and to 150 mg SC multiple dose panel. Nine (9), healthy subjects are assigned to the two IV cohorts (100 mg IV, or 750 mg IV).

Sixteen (16), healthy subjects are assigned to each of the dose panels that include a KLH immunization (30 mg SC, 100 mg SC or 300 mg SC). Within each KLH immunization dose panel, subjects are assigned in a 3:1 ratio to receive BMS-986090 (N=12) or placebo (N=4). Subjects in KLH panels who do not complete up to Day 15 assessments (except those discontinued for adverse events) are replaced. The planned dose for KLH challenge dose panels could be changed and an additional KLH cohort of 16 subjects might be added depending on results from interim analyses.

Each SC dose panels will have subjects assigned in 3:1 ratio to receive BMS-986090 (N=9/N=12) or placebo (N=3/N=4). Each IV dose panels will have subjects assigned in 2:1 ratio to receive BMS-986090 (N=6) or placebo (N=3).

Figure 4:
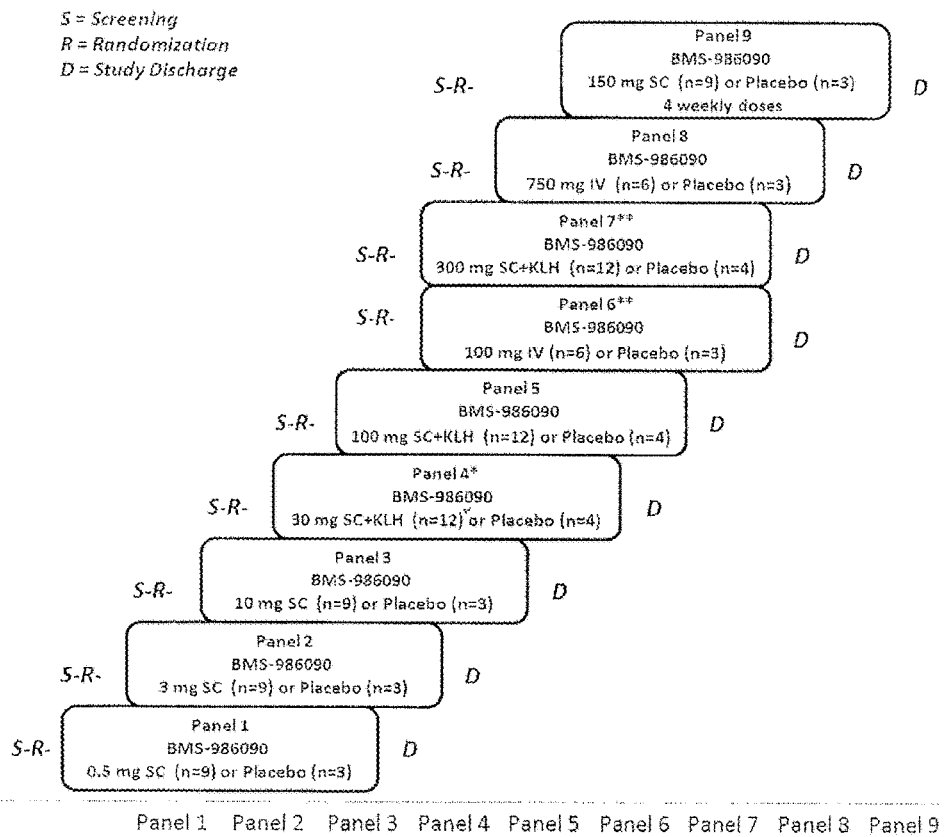
FIG. 4 depicts a study design schematic for a proposed clinical trial.

FIG. 4 depicts a study design schematic for the proposed dose panels. FIGS. 5A-5C depict treatment administration for the proposed dose panels.

Subjects in the single dose panels are admitted to the clinical facility on the morning of Day −1 and will remain in the clinic for 15 days for a total of 16 days in-house. Dosing of BMS-986090 or placebo will occur on Day 1. Safety PK and PD assessments are performed during the study. Subjects are furloughed from the clinical facility following completion of their study evaluation on approximately Day 15. Subjects with any ongoing adverse events (AE) or serious adverse events (SAE) at Day 15 should remain at the study site until the Investigator has determined that these events have been resolved or deemed as not clinically significant by the Investigator. Subjects will return to the facility on Day 22, Day 29, Day 43, Day 57, Day 71 and Day 85 for additional PK, immunogenicity, receptor occupancy (RO), PD and end of study safety assessments.

In the dose panels that include KLH immunization, KLH is administered immediately following BMS-986090 or placebo administration at a dose of 1.0 mg subcutaneously on Day 1 for all the subjects. Both total and KLH-specific immunoglobulin titers are measured before administration of BMS-986090 on Day 1, and on Day 8, Day 15, Day 22 and 29. All PK, immunogenicity, RO, PD and end of study safety assessments are identical to those of non KLH dose panels. BMS-986090 concentrations are measured at the time when blood samples for KLH assessment are collected.

Subjects in the multiple-dose panel are admitted to the clinical facility on the morning of Day −1 and will remain in the clinic for 29 days for a total of 30 days in-house. Each subject will receive a total of 4 doses of BMS-986090 or placebo, administered once a week by SC injection. Subjects are furloughed from the clinical facility following completion of their study evaluation on approximately Day 29. Subjects with any ongoing adverse events (AE) or serious adverse events (SAE) at Day 29 should remain at the study site until the Investigator has determined that these events have been resolved or deemed as not clinically significant by the Investigator. Subjects will return to the facility on, Day 43, Day 57, Day 71 and Day 85 for additional PK, immunogenicity, receptor occupancy (RO), PD and end of study safety assessments.

In all single dose panels (Panels 1-8; 0.5 mg SC, 3 mg SC, 10 mg SC, 30 mg SC, 100 mg SC, 100 mg IV, 300 mg SC, and 750 mg IV) there are two sentinel cohorts of 2 subjects each. On Day 1, one subject will receive BMS-986090 and another subject will receive a look a-like placebo in a blinded fashion. After review of the safety data, two additional subjects will receive their assigned treatments (one active and one placebo) on Day 3. Safety data (including any reported adverse events (AEs), findings from physical exams, any clinical laboratory results including analysis of the cytokines, vital signs and ECGs) from these 2 sentinel cohorts are evaluated by the Investigator and Sponsor prior to treatment of the remaining subjects in the respective dose panel on Day 5.

Dose escalation, will only occur after the Sponsor and the Investigator perform a satisfactory review of the preliminary safety data at the current dose level. Dose escalation will depend upon the clinical profile (evaluation of adverse events, vital signs, ECGs, and clinical laboratory parameters) of the doses up to and including the preceding dose group. Subjects will not be randomized at the next higher dose level until the safety data up to Day 15 for all subjects from the current dose level are reviewed by the Investigator and the Sponsor, and are determined to demonstrate safety and tolerability. If a dose level is found to be safe and tolerated, then the succeeding panel of 9 (for IV Panels), or 12 (for non-KLH panels) will receive the next higher dose of BMS-986090 or placebo. In additional to safety and tolerability assessment, the selection of dose for the KLH panel(s) is guided by a Bayesian model-based approach. Currently, KLH is planned for 30 mg, 100 mg & 300 mg SC and an additional KLH cohort of sixteen (16) healthy subjects might be added depending on results from Bayesian model-based interim analyses of data from first 5 dose levels. There is no intra-subject dose escalation.

The decision to stop dose escalation before treating the next panel is made if warranted by emerging safety events. Dose escalation to the next planned dose will not proceed if any of the following criteria are met (Adverse event grading as defined by the Common Terminology Criteria for Adverse Events {CTCAE, Version 4.03}). These criteria apply only to events that occurred in study subjects on the active medication (BMS-986090).

(1) Adverse Events:

Two subjects within dose level panel experience the same Grade 2 adverse event, determined to be at least possibly related to BMS-986090.

Occurrence within dose level panel of two Grade 2 infections determined to be at least possibly related to BMS-986090.

Occurrence within dose level panel of one opportunistic infection, including but not limited to *Mycobacterium avium* complex infection, tuberculosis, *Pneumocystis jirovecii* pneumonia, toxoplasmosis of brain, diffuse candidiasis, CMV disease, determined to be at least possibly related to BMS-986090.

Occurrence within dose level panel of Grade 2 cytokine release syndrome determined to be at least possibly related to BMS-986090.

(2) Abnormal Laboratory Results:

Occurrence of one or more significant changes within a dose level panel in hepatic function, defined as alanine aminotransferase (ALT) or aspartate aminotransferase (AST) >3 times the upper limit of normal (ULN) associated with bilirubin >2×ULN.

Occurrence of two cases of AST or ALT >5×ULN, or a single ALT elevation of >10×ULN in the absence of alternate explanation.

In addition, the Sponsor and Investigator may decide to halt dose escalation for reasons not defined above, including but not limited to, observing a single serious adverse event in individual subjects and/or observing trends in a given dose panel and across dose panels.

The review of the safety data will include unblinding of the subject(s) that experienced AEs listed above. In addition, the unblinded data set may include subjects from a dose panel, the entire dose panel, or if appropriate, all randomized subjects treated to date. Unblinding recommendation must be approved by the sponsor's medical monitor.

If at any dose level, the stopping criteria are met, the next higher dose level will not be administered, but a lower dose level may be investigated. For example, if the study is stopped at the 300 mg SC dose level, then 200 mg SC may be studied. If the study is stopped at the 100 mg SC dose level, 60 mg SC may be studied.

In addition, after the first five panels, the selection of KLH panel doses is guided by a Bayesian model-based approach as discussed below. Bayesian probability is a probability theory that starts with a prior belief based on existing knowledge (e.g. modeling and estimation), and evaluates posterior probabilities based on actual data collected in the study. If the posterior probability of pre-specified parameters are achieved (e.g. estimated PK/PD for pre-specified doses are achieved), then the pre-specified dose is used in the next cohort; otherwise, a new dose is calculated using PK/PD parameters.

In this study, three KLH challenge dose levels (30 mg, 100 mg & 300 mg SC) are planned to explore the potential possibility of an exposure/dose response of KLH. The 300 mg SC is expected to provide significant KLH suppression, while the other two KLH dose panels are expected to provide less KLH suppression. The first and second KLH challenges are done for 30 mg and 100 mg dose levels, respectively. The third KLH challenge is planned for 300 mg SC. An additional cohort might be added before or after 300 mg SC dose panel based on assessment of previous dose panels KLH data and dose-response Bayesian Emax model fitted on RO data. Model is first fit to the accrued Receptor Occupancy (RO) week 1 (hour 168) data from panels 1 to 5 and Bayesian posterior probabilities are derived to guide next KLH panel dose selection. The projected receptor occupancy (RO) is displayed in FIG. 3 and is used as clinical threshold for dose selection.

The following criteria are used to proceed to KLH immunization dose levels:

If first KLH dose panel (30 mg SC) show negligible suppression at two weeks and 100 mg SC shows 100% suppression at two weeks then an additional KLH cohort with dose between 30 & 100 mg is selected as guided by dose-response (RO) Bayesian Emax model. The fourth KLH dose panel is 300 mg SC but might not be tested for KLH suppression depending on KLH & RO data from previous dose panels.

if first KLH dose panel (30 mg SC) show negligible suppression at two weeks and 100 mg SC shows less than 100% suppression at two weeks then third KLH is done for 300 mg SC dose panel. The fourth KLH cohort might be added based on KLH data from 30, 100 & 300 mg SC dose panels and from the dose-response Bayesian Emax model fitted on RO data.

If first (30 mg SC) and second (100 mg SC) KLH dose panels show 100% suppression at two weeks then additional KLH cohort with dose less than 30 mg SC might be added as guided by dose-response (RO) Bayesian Emax model. The 300 mg SC might not be tested for KLH suppression depending on KLH and RO data from previous dose panels.

Dose panels that include KLH challenge could be modified and an additional KLH cohort of 16 subjects might be added depending on results from interim analyses. For example, if the median observed RO at Cmax of 10 mg SC (the previous cohort to 30 mg SC the starting cohort of KLH) is less than 90%, KLH may not be studied for 30 mg SC, and 12 instead of 16 subjects are dosed in this cohort for safety, PK and PD evaluation.

The operating characteristics of the proposed approach were studied by simulations. In the simulations, n=9 subjects are dosed with BMS-986090 for each cohort and Receptor occupancy data was generated according to three scenarios. Markov chain Monte Carlo (MCMC) was used to simulate samples from posterior distribution of parameters and update the parameters utilizing accumulated available data. The priors for the Emax model parameters for Receptor occupancy were obtained from internal preclinical data. Normal distributions are used for the prior distributions of E0 and Emax and uniform distribution is used for the prior distribution of ED50.

Physical examinations, vital sign measurements, 12-lead electrocardiograms (ECG), and clinical laboratory evaluations are performed at selected times throughout the dosing interval. Subjects are closely monitored for adverse events throughout the study. Blood is collected for up to 2016 hours after study drug administration for pharmacokinetic (PK) analysis. Approximately 671 mL of blood are drawn from each subject in the single dose panel, and approximately 757 mL of blood are drawn from each subject in the multiple dose panel during the study. From the total amount of blood drawn during the study, approximately 174 mL of blood are collected in the first 48-hour period.

The approximate duration of the study is 113 days (28 day screening and 85 days on study). The date the first subject is enrolled is defined as the start of the study. A subject is considered enrolled when the study specific informed consent is signed. The date that the last subject completes the discharge procedures is defined as the "last visit." The date of the last visit of the last subject undergoing the study is defined as the "end of the study."

Target Population

The target population for this study is healthy male and female subjects as determined by no clinically significant deviation from normal in medical history, physical examination, ECGs, and clinical laboratory determinations. Women of childbearing potential (WOCBP) must follow instructions for birth control. Subjects will have a Body Mass Index (BMI) of 18 to 32 kg/m$^2$, inclusive, {BMI=weight (kg)/[height (m)]$^2$}, and total body weight >50 kg (110 lb). (BMI may be rounded down, e.g. a subject with a BMI of 32.4 would qualify). Regarding age and reproductive status, the target population is men and women, ages 18 to 45 years, inclusive. Women must have a negative serum or urine pregnancy test (minimum sensitivity 25 IU/L or equivalent units of HCG) within 24 hours prior to the start of study drug. Women must not be breastfeeding. Men who are sexually active with WOCBP must agree to follow instructions for method(s) of contraception for the duration of treatment plus 5 half-lives of the study drug (85 days) plus 90 days (duration of sperm turnover) for a total of 175 days post-treatment completion. Azoospermic males and WOCBP who are continuously not heterosexually active are exempt from contraceptive requirements.

Exclusion Criteria

Exclusion criteria include: history of thrombophilia, venous or arterial thromboembolism (VTE or ATE), including history of myocardial infarction (MI), cerebrovascular accident (CVA), pulmonary embolism (PE), deep vein thrombosis (DVT). Exclusion criteria further include; Known or suspected autoimmune disorder, including but not limited to rheumatoid arthritis, fibromyalgia, systemic lupus erythematosis, polymyalgia rheumatica, giant cell arteritis, Behcet's disease, dermatomyositis, multiple sclerosis, moderate to severe asthma, any autoimmune vasculitis, autoimmune hepatitis, or any other active autoimmune disease for which a subject requires medical follow-up or medical treatment.

Pharmacokinetic Assessments

Pharmacokinetics of BMS-986090 are derived from serum concentration versus time data. The pharmacokinetic parameters to be assessed include:

| | |
|---|---|
| Cmax | Maximum observed serum concentration |
| Tmax | Time of maximum observed serum concentration |
| AUC(0-T) | Area under the serum concentration-time curve from time zero to time of last quantifiable concentration (Single Dose Only) |
| AUC(INF) | Area under the serum concentration-time curve from time zero extrapolated to infinite time (Single Dose Only) |
| T-HALF | Terminal serum half-life |
| CLT | Total body clearance (IV only) |
| CLT/F | Apparent total body clearance (SC only) |
| Vz | Volume of distribution at terminal phase (IV only) |
| Vss | Volume of distribution during steady state (IV only) |
| Vz/F | Apparent volume of distribution at terminal phase (SC only) |
| F | Absolute bioavailability (SC only) |
| AUC(TAU) | Area under the serum concentration-time curve in one dosing Interval (Multiple Dose only) |
| Ctrough | Trough observed plasma concentration (Multiple Dose only) |
| Css-avg | Average concentration over a dosing interval (Multiple Dose only) |
| DF | Degree of Fluctuation (Multiple Dose only) |
| AI_AUC | AUC Accumulation Index; ratio of AUC (TAU) at steady state to AUC (TAU) after the first dose (Multiple Dose only) |
| AI_Cmax | Cmax Accumulation Index; ratio of Cmax at steady state to Cmax after the first dose (Multiple Dose only) |

Individual subject pharmacokinetic parameter values are derived by non compartmental methods by a validated pharmacokinetic analysis program. Actual times are used for the analyses.

Primary Biomarker Assessments (1) Receptor Occupancy

Receptor occupancy on B cells and other peripheral target cells is measured over time as a biomarker of target engagement. Blood is drawn in the appropriate collection tubes before and after treatment for the analytical assessments. Receptor occupancy is assessed on B cells and other target cells using a validated flow cytometry based assay.

(2) Anti-KLH Titers

For cohorts with KLH antigen immunization, the relative levels of anti-KLH IgG and IgM are measured after single dosing of BMS-986090. Blood is drawn in the appropriate collection tubes before and after treatment. Serum is shipped to the central laboratory and tested in a validated immunoassay for the measurement of anti-KLH specific IgG and IgM antibodies. Total IgM and IgG are measured to reference changes in overall Ig levels.

Primary Endpoint(s)

The primary objective relates to the safety and tolerability of a single dose of BMS-986090. The primary safety endpoint is the incidence, potential significance, and clinical importance of adverse events measured up to 85 days after single dose of BMS-986090, as determined by medical review of adverse event reports, vital sign measurements, electrocardiograms (ECGs), and results of physical examination and laboratory tests.

Secondary Endpoint(s)

The first secondary objective to assess the single dose PK of BMS-986090 administered as a SC and IV formulation is measured by the following secondary endpoints:

Cmax, Tmax, AUC(0-T), AUC(INF), T-HALF, CLT (IV only), CLT/F (SC only), Vz (IV only), Vss OV only), Vz/F (SC only), and F (SC only).

The second secondary objective to assess the multiple dose PK of BMS-986090 administered as a SC formulation is measured by the following secondary endpoints:

Cmax, Tmax, T-HALF, AUC(TAU), Ctrough, Css-avg, DF, AI_AUC, AI_Cmax, CLT/F, DF.

The third secondary objective to assess the inhibitory effect of BMS-986090 on KLH induced Ig response following a single SC injection ise measured by the following secondary endpoints of anti-KLH IgG and IgM antibody levels at specific time points.

The fourth secondary objective to assess the immunogenicity of BMS-986090 following single SC or IV infusion is measured by:

Frequency of subjects with positive anti-drug-antibody (ADA) assessment;

Frequency of subjects who develop positive ADA following a negative baseline.

The assessments are done at specific time points.

The fifth secondary objective to assess the level of target engagement (receptor occupancy) of BMS-986090 following single SC or IV administration is measured by receptor occupancy (RO) at specific time points.

Exploratory Biomarker Measures

Serum cytokines and other pro-inflammatory proteins are measured to monitor for evidence of immune activation and will include, but not be limited to IL-1β, IL-2, IL-6, IL-8, IL-12, IFN-γ, TNFα and soluble adhesion molecules (sICAM and sVCAM). Peripheral T, B and NK cell counts (T/B/NK panel) are measured to monitor peripheral cell populations. Functional PD assays will measure the inhibition of peripheral functional responses by BMS-986090 following ex vivo CD40L treatment using flow cytometry and mRNA methodologies.

Phase 2

Phase 2 is a proof of concept (POC) study in subjects with ulcerative colitis (UC). Efficacious dose ranges established in Phase 1 applying results from pharmacodynamic (PD) and proof of mechanism (POM) biomarker assessments are studied.

ABBREVIATIONS

Table 5 lists abbreviations that may be used in the present Example.

TABLE 5

| Term | Definition |
| --- | --- |
| AE | adverse event |
| AI | accumulation index |
| AI_AUC | AUC Accumulation Index; ratio of AUC(TAU) at steady state to AUC(TAU) after the first dose |
| AI_Cmax | Cmax Accumulation Index; ratio of Cmax at steady state to Cmax after the first dose |
| AI_Ctau | Ctau Accumulation Index; ratio of Ctau at steady state to Ctau after the first dose |
| ANC | absolute neutrophil count |
| ANOVA | analysis of variance |
| AUC | area under the concentration-time curve |
| AUC(INF) | area under the concentration-time curve from time zero extrapolated to infinite time |
| AUC(0-T) | area under the concentration-time curve from time zero to the time of the last quantifiable concentration |
| AUC(TAU) | area under the concentration-time curve in one dosing interval |
| A-V | atrioventricular |
| BP | blood pressure |
| C | Celsius |
| C12 | concentration at 12 hours |
| C24 | concentration at 24 hours |
| Cavg | average concentration |
| CBC | complete blood count |
| Cexpected-tau | expected concentration in a dosing interval |
| CI | confidence interval |
| CLT | total body clearance |
| CLT/F (or CLT) | apparent total body clearance |
| CLT/F/fu or CLT/fu | Apparent clearance of free drug or clearance of free if (if IV) |
| Cm | centimeter |
| Cmax, CMAX | maximum observed concentration |
| Cmin, CMIN | trough observed concentration |
| Ct | Expected concentration at a certain time, usually at the end of an expected future dosing interval (eg, concentration at 24 hours, concentration at 12 hours, etc.) |
| Ctau | Concentration in a dosing interval (eg, concentration at 24 hours, concentration at 12 hours, etc.) |
| Ctrough | Trough observed plasma concentration |
| CV | coefficient of variation |
| EA | extent of absorption |
| F | bioavailability |
| Fb | fraction of bound drug |
| FI | fluctuation Index ([Cmax − Ctau]/Cavg]) |
| Fu | fraction of unbound drug |
| GC | gas chromatography |
| GFR | glomerular filtration rate |
| IU | International Unit |
| IV | Intravenous |
| K | slope of the terminal phase of the log concentration-time curve |
| LC | liquid chromatography |
| MTD | maximum tolerated dose |
| μg | Microgram |
| N | number of subjects or observations |
| N/A | not applicable |
| PD | Pharmacodynamics |
| PK | Pharmacokinetics |
| PO | per os (by mouth route of administration) |
| PT | prothrombin time |
| PTT | partial thromboplastin time |
| Pu | percent of unbound drug |
| $R^2$ | coefficient of determination |
| SAE | serious adverse event |
| SD | standard deviation |
| sp. | Species |
| T-HALF | Half life |
| T-HALFeff_AUC | Effective elimination half life that explains the degree of AUC accumulation observed |
| T-HALFeff_Cmax | Effective elimination half life that explains the degree of Cmax accumulation observed) |
| Tmax, TMAX | time of maximum observed concentration |

TABLE 5-continued

| Term | Definition |
| --- | --- |
| TR_AUC(0-T) | AUC(0-T) treatment ratio |
| TR_AUC(INF) | AUC(INF) treatment ratio |
| TR_Cmax | Cmax treatment ratio |
| UC | Ulcerative colitis |

Although the present embodiments have been described in detail with reference to examples above, it is understood that various modifications can be made without departing from the spirit of these embodiments, and would be readily known to the skilled artisan.

What is claimed is:

1. A method of treating an inflammatory bowel disease (IBD) in a human patient, the method comprising administering to the patient at least one dose of an antibody polypeptide comprising
    (1) a variable domain Wherein the amino acid sequence of the variable domain comprises BMS3h-56-269 (SEQ ID NO: 1) or comprises (a) a CDR1 region consisting of amino acids 31 to 35 of BMS3h-56-269 as shown in SEQ ID NO: 1, (b) a CDR2 region consisting of amino acids 50 to 66 of BMS3h-56-269 as shown in SEQ ID NO: 1, and (c) a CDR3 region consisting of amino acids 99 to 105 of BMS3h-56-269 as shown in SEQ NO: 1, and
    (2) a human Fc domain,
    and the dose is selected from 0.5 to 300 milligrams of the antibody polypeptide for sub-cutaneous administration or from 100 to 750 mg of the antibody polypeptide for intravenous administration.

2. The method of claim 1, wherein the administration is sub-cutaneous and the dose is selected from 0.5, 3, 10, 30, 100, 150, or 300 mg of the antibody polypeptide.

3. The method of claim 1, wherein the administration is sub-cutaneous, the dose is from 150 to 300 mg of the antibody polypeptide, and the method comprises at least four iterations of the administering step.

4. The method of claim 1, wherein the administration is intravenous and the dose is selected from 100 or 750 mg of the antibody polypeptide.

5. The method of claim 1, wherein the antibody polypeptide is administered in combination with an immunosuppressive/immunomodulatory and/or anti-inflammatory agent.

6. The method of claim 5, wherein the antibody polypeptide and the immunosuppressive/immunomodulatory and/or anti-inflammatory agent are administered sequentially.

7. The method of claim 5, wherein the antibody polypeptide and the immunosuppressive/immunomodulatory and/or anti-inflammatory agent are administered simultaneously.

8. The method of claim 7, Wherein the antibody polypeptide and the immunosuppressive/immunomodulatory and/or anti-inflammatory agent are formulated in a single composition.

9. The method of claim 1, wherein the IBD is selected from the group consisting of: colitis, Crohn's disease and Behcet's disease.

10. The method of claim 9, Wherein the colitis is selected from the group consisting of ulcerative colitis, collagenous colitis, lymphocytic colitis, and diversion colitis.

11. The method of claim 1, wherein the Fc domain comprises an amino acid sequence selected from SEQ ID NO: 4 or SEQ ID NO: 6.

12. The method of claim 1, wherein the antibody polypeptide further comprises a linker selected from the group consisting of: SEQ ID NOS: 8-16.

13. The method of claim 1, wherein the amino acid sequence of the variable domain comprises BMS3h-56-269 (SEQ ID NO: 1).

14. The method of claim 13, wherein the Fc domain (region) comprises the amino acid sequence of SEQ ID NO: 6.

15. The method of claim 1, wherein the antibody polypeptide comprises the amino acid sequence of SEQ ID NO: 7.

16. The method of claim 1, wherein the antibody polypeptide is linked to one or more PEG polymers.

* * * * *

UNITED STATES PATENT AND TRADEMARK OFFICE
CERTIFICATE OF CORRECTION

Page 1 of 1

PATENT NO. : 10,435,475 B2
APPLICATION NO. : 15/118279
DATED : October 8, 2019
INVENTOR(S) : Marek Honczarenko et al.

It is certified that error appears in the above-identified patent and that said Letters Patent is hereby corrected as shown below:

In the Claims

At Column 49, Claim number 1, Line number 33, "Wherein" should read --wherein--

At Column 49, Claim number 1, Line numbers 40-41, "SEQ NO: 1" should read --SEQ ID NO: 1--

At Column 49, Claim number 1, Line number 42, "Fe" should read --Fc--

At Column 49, Claim number 1, Line number 43, "milligrams of" should read "milligrams (mg) of"--

At Column 50, Claim number 8, Line number 33, "Wherein" should read --wherein--

At Column 50, Claim number 10, Line number 40, "Wherein" should read --wherein--

Signed and Sealed this
Seventh Day of January, 2020

Andrei Iancu
*Director of the United States Patent and Trademark Office*

```
                       SEQUENCE LISTING

<160> NUMBER OF SEQ ID NOS: 23

<210> SEQ ID NO 1
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Glu Met Trp Trp Val Arg Gln Ala Pro Gly Lys Gly Leu Glu Arg Val
        35                  40                  45

Ser Ala Ile Asn Pro Gln Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Phe Arg Phe Ser Asp Arg Gly Gln Gly Thr Leu Val
            100                 105                 110

Thr Val Ser Ser
        115

<210> SEQ ID NO 2
<211> LENGTH: 348
<212> TYPE: DNA
<213> ORGANISM: Artificial
<220> FEATURE:
<223> OTHER INFORMATION: Description of Artificial Sequence: Synthetic
      polypnucleotide

<400> SEQUENCE: 2
gaggtgcagc tgttggagtc tgggggaggc ttggtacagc ctgggggtc cctgcgtctc      60 tcctgtgcag cctccggatt cacctttcgg gattatgaga tgtggtgggt ccgccaggct    120
ccagggaagg gtctagagcg ggtctcagct attaatccgc agggtacgcg tacatactac    180
gcagactccg tgaagggccg gttcaccatc tcccgcgaca attccaagaa cacgctgtat    240
ctgcaaatga acagcctgcg tgccgaggat accgcggtat attactgtgc gaaacttccg    300
tttaggtttt ccgaccgggg tcagggaacc ctggtcaccg tctcgagc                 348
```

-continued

<210> SEQ ID NO 3
<211> LENGTH: 277
<212> TYPE: PRT
<213> ORGANISM: Homo sapiens

<400> SEQUENCE: 3

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 4
<211> LENGTH: 229
<212> TYPE: PRT
<213> ORGANISM: Artificial
<220> FEATURE:
<223> OTHER INFORMATION: Description of Artificial Sequence: Synthetic
      polypeptide

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val

```
                      35                  40                  45
Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 5
<211> LENGTH: 348
<212> TYPE: PRT
<213> ORGANISM: Artificial
<220> FEATURE:
<223> OTHER INFORMATION: Description of Artificial Sequence: Synthetic
      polypeptide

<400> SEQUENCE: 5

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Asp Tyr
                20                  25                  30

Glu Met Trp Trp Val Arg Gln Ala Pro Gly Lys Gly Leu Glu Arg Val
            35                  40                  45

Ser Ala Ile Asn Pro Gln Gly Thr Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Pro Phe Arg Phe Ser Asp Arg Gly Gln Gly Thr Leu Val
                100                 105                 110

Thr Val Ser Ser Ala Ser Thr Glu Ser Lys Tyr Gly Pro Pro Cys Pro
            115                 120                 125

Pro Cys Pro Ala Pro Glu Phe Leu Gly Gly Pro Ser Val Phe Leu Phe
        130                 135                 140

Pro Pro Lys Pro Lys Asp Thr Leu Met Ile Ser Arg Thr Pro Glu Val
145                 150                 155                 160
```

```
Thr Cys Val Val Val Asp Val Ser Gln Glu Asp Pro Glu Val Gln Phe
                165                 170                 175
Asn Trp Tyr Val Asp Gly Val Glu Val His Asn Ala Lys Thr Lys Pro
            180                 185                 190
Arg Glu Glu Gln Phe Asn Ser Thr Tyr Arg Val Val Ser Val Leu Thr
        195                 200                 205
Val Leu His Gln Asp Trp Leu Asn Gly Lys Glu Tyr Lys Cys Lys Val
    210                 215                 220
Ser Asn Lys Gly Leu Pro Ser Ser Ile Glu Thr Ile Ser Lys Ala
225                 230                 235                 240
Lys Gly Gln Pro Arg Glu Pro Gln Val Tyr Thr Leu Pro Pro Ser Gln
                245                 250                 255
Glu Glu Met Thr Lys Asn Gln Val Ser Leu Thr Cys Leu Val Lys Gly
            260                 265                 270
Phe Tyr Pro Ser Asp Ile Ala Val Glu Trp Glu Ser Asn Gly Gln Pro
        275                 280                 285
Glu Asn Asn Tyr Lys Thr Thr Pro Pro Val Leu Asp Ser Asp Gly Ser
    290                 295                 300
Phe Phe Leu Tyr Ser Arg Leu Thr Val Asp Lys Ser Arg Trp Gln Glu
305                 310                 315                 320
Gly Asn Val Phe Ser Cys Ser Val Met His Glu Ala Leu His Asn His
                325                 330                 335
Tyr Thr Gln Lys Ser Leu Ser Leu Ser Leu Gly Lys
            340                 345

<210> SEQ ID NO 6
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Pro Lys Ser Ser Asp Lys Thr His Thr Ser Pro Pro Ser Pro Ala
1               5                   10                  15
Pro Glu Leu Leu Gly Gly Ser Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Asp Glu Leu Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 7
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Glu Met Trp Trp Val Arg Gln Ala Pro Gly Lys Gly Leu Glu Arg Val
        35                  40                  45

Ser Ala Ile Asn Pro Gln Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Phe Arg Phe Ser Asp Arg Gly Gln Gly Thr Leu Val
            100                 105                 110

Thr Val Ser Ser Ala Ser Thr Glu Pro Lys Ser Ser Asp Lys Thr His
        115                 120                 125

Thr Ser Pro Pro Ser Pro Ala Pro Glu Leu Leu Gly Gly Ser Ser Val
130                 135                 140

Phe Leu Phe Pro Pro Lys Pro Lys Asp Thr Leu Met Ile Ser Arg Thr
145                 150                 155                 160

Pro Glu Val Thr Cys Val Val Asp Val Ser His Glu Asp Pro Glu
                165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Arg Asp Glu Leu Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
```

```
                290             295             300
Asp Gly Ser Phe Phe Leu Tyr Ser Lys Leu Thr Val Asp Lys Ser Arg
305                 310             315                 320

Trp Gln Gln Gly Asn Val Phe Ser Cys Ser Val Met His Glu Ala Leu
                325             330             335

His Asn His Tyr Thr Gln Lys Ser Leu Ser Leu Ser Pro Gly Lys
            340             345             350
```

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Gly Gly Gly Gly Ser
1               5
```

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Gly Gly Gly Gly Ser Gly Gly Gly Gly Ser
1               5                   10
```

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Gly Gly Gly Gly Ser Gly Gly Gly Gly Ser Gly Gly Gly Gly Ser
1               5                   10                  15
```

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 12

Gly Gly Gly Gly Ser Gly Gly Gly Ser Gly Gly Gly Gly Ser Gly
1               5                   10                  15

Gly Gly Gly Ser Gly Gly Gly Ser
            20                  25

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Ser Thr
1

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Thr Val Ala Ala Pro Ser
1               5

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Thr Val Ala
1

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Ser Thr Ser Gly Pro Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (1)..(1)
<223> OTHER INFORMATION: Asp or Gly
<220> FEATURE:
<221> NAME/KEY: VARIANT
<222> LOCATION: (4)..(4)
```

<223> OTHER INFORMATION: Met or Leu

<400> SEQUENCE: 17

Xaa Tyr Glu Xaa Trp
1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (5)..(5)
<223> OTHER INFORMATION: Gln, Tyr, Pro, Trp or Ala
<220> FEATURE:
<221> NAME/KEY: VARIANT
<222> LOCATION: (7)..(7)
<223> OTHER INFORMATION: Thr, Ser, Asn, Gly, Met or Gln
<220> FEATURE:
<221> NAME/KEY: VARIANT
<222> LOCATION: (8)..(8)
<223> OTHER INFORMATION: Arg, Leu, Tyr, His or Phe
<220> FEATURE:
<221> NAME/KEY: VARIANT
<222> LOCATION: (16)..(16)
<223> OTHER INFORMATION: Lys or Met

<400> SEQUENCE: 18

Ala Ile Asn Pro Xaa Gly Xaa Xaa Thr Tyr Tyr Ala Asp Ser Val Xaa
1               5                   10                  15

Gly

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (1)..(1)
<223> OTHER INFORMATION: Leu or Pro
<220> FEATURE:
<221> NAME/KEY: VARIANT
<222> LOCATION: (3)..(3)
<223> OTHER INFORMATION: Phe, Gln, Thr or Met
<220> FEATURE:
<221> NAME/KEY: VARIANT
<222> LOCATION: (4)..(4)
<223> OTHER INFORMATION: Tyr, Pro, Leu, Thr, Ile, Phe or Met
<220> FEATURE:
<221> NAME/KEY: VARIANT
<222> LOCATION: (6)..(6)
<223> OTHER INFORMATION: Gln, His, Asp, Ser, Lys, Glu or Gly
<220> FEATURE:
<221> NAME/KEY: VARIANT
<222> LOCATION: (7)..(7)
<223> OTHER INFORMATION: Glu, Asp or Tyr

<400> SEQUENCE: 19

Xaa Pro Xaa Xaa Phe Xaa Xaa
1               5

<210> SEQ ID NO 20
<211> LENGTH: 30
<212> TYPE: PRT
<213> ORGANISM: Artificial Sequence
<220> FEATURE:

```
<223> OTHER INFORMATION: Description of Artificial Sequence: Synthetic
      Polypeptide
<220> FEATURE:
<221> NAME/KEY: VARIANT
<222> LOCATION: (18)..(18)
<223> OTHER INFORMATION: Leu or Arg
<220> FEATURE:
<221> NAME/KEY: VARIANT
<222> LOCATION: (30)..(30)
<223> OTHER INFORMATION: Arg or Ala

<400> SEQUENCE: 20

Glu Val Gln Leu Leu Glu Ser Gly Gly Gly Leu Val Gln Pro Gly Gly
1               5                   10                  15

Ser Xaa Arg Leu Ser Cys Ala Ala Ser Gly Phe Thr Phe Xaa
            20                  25                  30

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (4)..(4)
<223> OTHER INFORMATION: Gln or Arg
<220> FEATURE:
<221> NAME/KEY: VARIANT
<222> LOCATION: (8)..(8)
<223> OTHER INFORMATION: Lys or Arg
<220> FEATURE:
<221> NAME/KEY: VARIANT
<222> LOCATION: (9)..(9)
<223> OTHER INFORMATION: Gly or Val

<400> SEQUENCE: 21

Trp Val Arg Xaa Ala Pro Gly Xaa Xaa Leu Glu Arg Val Ser
1               5                   10

<210> SEQ ID NO 22
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (12)..(12)
<223> OTHER INFORMATION: Thr or Met
<220> FEATURE:
<221> NAME/KEY: VARIANT
<222> LOCATION: (23)..(23)
<223> OTHER INFORMATION: Glu or Asp
<220> FEATURE:
<221> NAME/KEY: VARIANT
<222> LOCATION: (26)..(26)
<223> OTHER INFORMATION: Ala or Ser
<220> FEATURE:
<221> NAME/KEY: VARIANT
<222> LOCATION: (29)..(29)
<223> OTHER INFORMATION: Tyr or His
<220> FEATURE:
<221> NAME/KEY: VARIANT
<222> LOCATION: (31)..(31)
<223> OTHER INFORMATION: Ala or Thr

<400> SEQUENCE: 22

Arg Phe Thr Ile Ser Arg Asp Asn Ser Lys Asn Xaa Lys Tyr Leu Gln
1               5                   10                  15
```

```
Met Asn Ser Leu Arg Ala Xaa Asp Thr Xaa Val Tyr Xaa Cys Xaa Lys
            20                  25                  30

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (1)..(1)
<223> OTHER INFORMATION: Trp or Arg
<220> FEATURE:
<221> NAME/KEY: VARIANT
<222> LOCATION: (3)..(3)
<223> OTHER INFORMATION: Gln or Pro
<220> FEATURE:
<221> NAME/KEY: VARIANT
<222> LOCATION: (11)..(11)
<223> OTHER INFORMATION: Ser or Asn

<400> SEQUENCE: 23

Xaa Gly Xaa Gly Thr Leu Val Thr Val Ser Xaa
1               5                   10
```